United States Patent
Narendran et al.

(10) Patent No.: US 11,938,182 B2
(45) Date of Patent: *Mar. 26, 2024

(54) HALOGENATED XANTHENES AS VACCINE ADJUVANTS

(71) Applicants: Provectus Pharmatech, Inc., Knoxville, TN (US); UTI Limited Partnership, Calgary (CA)

(72) Inventors: Aru Narendran, Calgary (CA); Dominic Rodrigues, Knoxville, TN (US); Edward V. Pershing, Knoxville, TN (US); Bruce Horowitz, Knoxville, TN (US)

(73) Assignees: Provectus Pharmatech, Inc., Knoxville, TN (US); UTI Limited Partnership, Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/488,430

(22) Filed: Sep. 29, 2021

(65) Prior Publication Data

US 2022/0016242 A1  Jan. 20, 2022

Related U.S. Application Data

(63) Continuation-in-part of application No. 17/212,723, filed on Mar. 25, 2021.

(60) Provisional application No. 63/000,231, filed on Mar. 26, 2020.

(51) Int. Cl.
  *A61K 39/39* (2006.01)
  *A61K 39/00* (2006.01)

(52) U.S. Cl.
  CPC .......... *A61K 39/39* (2013.01); *A61K 39/0011* (2013.01); *A61K 2039/55511* (2013.01)

(58) Field of Classification Search
  CPC .............. A61K 39/39; A61K 39/0011; A61K 2039/55511; C12N 2730/10134
  See application file for complete search history.

(56) References Cited

U.S. PATENT DOCUMENTS

| | | | |
|---|---|---|---|
| 4,544,500 A | 10/1985 | Bittle et al. | |
| 4,599,231 A | 7/1986 | Milich et al. | |
| 4,625,015 A | 11/1986 | Green et al. | |
| 5,180,806 A | 1/1993 | Dillner et al. | |
| 5,998,597 A | 12/1999 | Fisher et al. | |
| 6,231,864 B1 | 5/2001 | Birkett | |
| 6,331,286 B1 | 12/2001 | Dees et al. | |
| 6,493,570 B1 | 12/2002 | Dees et al. | |
| 6,942,866 B2 | 9/2005 | Birkett | |
| 7,390,668 B2 | 6/2008 | Dees et al. | |
| 7,648,695 B2 | 1/2010 | Dees et al. | |
| 8,017,127 B2 | 9/2011 | Birkett | |
| 8,530,675 B2 | 9/2013 | Singer et al. | |
| 8,557,298 B2 | 10/2013 | Scott et al. | |
| 8,974,363 B2 | 3/2015 | Dees et al. | |
| 9,107,887 B2 | 8/2015 | Eagle et al. | |
| 9,273,022 B2 | 3/2016 | Singer et al. | |
| 9,422,260 B2 | 8/2016 | Singer et al. | |
| 9,808,524 B2 | 11/2017 | Eagle et al. | |
| 9,839,688 B2 | 12/2017 | Eagle et al. | |
| 10,130,658 B2 | 11/2018 | Singer et al. | |
| 10,471,144 B2 | 11/2019 | Eagle et al. | |
| 11,058,664 B2 | 7/2021 | Singer et al. | |
| 2002/0022032 A1* | 2/2002 | Curry | A61K 41/0057 424/183.1 |
| 2002/0150541 A1* | 10/2002 | Lau | A61K 38/212 424/46 |
| 2009/0117199 A1 | 5/2009 | Scott et al. | |
| 2012/0263677 A1* | 10/2012 | Eagle | A61K 38/217 514/266.22 |

(Continued)

FOREIGN PATENT DOCUMENTS

| | | |
|---|---|---|
| JP | 4507403 A | 12/1992 |
| JP | 2004503592 A | 2/2004 |
| JP | 2014510728 A | 5/2014 |

(Continued)

OTHER PUBLICATIONS

Berger et al. Trends in Molecular Medicine, May 2019, vol. 25, No. 5. (Year: 2019).*
"Immunogen." Merriam-Webster.com Dictionary, Merriam-Webster, https://www.merriam-webster.com/dictionary/immunogen. Accessed Apr. 27, 2023 (Year: 2023).*
Swift. OncoTargets and Therapy, Dec. 2019, 1293-1307 (Year: 2019).*
Berger, G. et al., "Pharmacological Modulation of the STING Pathway for Cancer Immunotherapy," Trends in Molecular Medicine, vol. 25, No. 5, May 2019, pp. 412-427.
International Search Report re application No. PCT/US21/52506, dated Jan. 14, 2022.

(Continued)

*Primary Examiner* — Susanna Moore
*Assistant Examiner* — Luisalberto Gonzalez
(74) *Attorney, Agent, or Firm* — Husch Blackwell LLP

(57) ABSTRACT

A method of inducing a Type I interferon response in a mammalian subject that presents with a microbial infection, cancerous tumor or hematological malignancy that comprises administering an amount of a halogenated xanthene as discussed above, effective to induce the Type I interferon response. A method of enhancing a mammalian immunogen-specific immune response that comprises contacting mammalian cells, in vivo or present in a mammalian cell growth supporting medium, with an adjuvant-effective amount of a halogenated xanthene, and an immunogen to which that response is to be enhanced. A mammalian HX compound-adjuvanted vaccine composition that contains an immunogen present in a vaccine-effective amount along with an adjuvant-effective amount of a halogenated xanthene (HX) compound and one or more excipients present at about 0.001% by weight to 10% by weight of the vaccine composition dissolved or dispersed in a pharmaceutically acceptable diluent.

9 Claims, 14 Drawing Sheets

(56) References Cited

U.S. PATENT DOCUMENTS

| | | |
|---|---|---|
| 2017/0173079 A1 | 6/2017 | Singer et al. |
| 2021/0299055 A1 | 9/2021 | Wachter et al. |

FOREIGN PATENT DOCUMENTS

| | | |
|---|---|---|
| WO | 90/13296 A1 | 11/1990 |
| WO | 2020028532 A1 | 2/2020 |
| WO | 2021/195400 A1 | 9/2021 |
| WO | 2021195573 A1 | 9/2021 |

OTHER PUBLICATIONS

Written Opinion re application No. PCT/US21/52506, dated Jan. 14, 2022.

Beutler, B. "Innate Immunity: An Overview," Molecular Immunology, vol. 40, pp. 845-859, (2004). doi:10.1016/j.molimm.2003.10.005.

Hoebe, K. et al, "The Interface Between Innate and Adaptive Immunity," Nature Immunology, vol. 5, No. 10, pp. 971-974 (Oct. 2004).

Fowlkes, A. et al, "Effectiveness of COVID-19 Vaccines in Preventing SARS-CoV-2 Infection Among Frontline Workers Before and During B.1.617.2 (Delta) Variant Predominance—Eight U.S. Locations, Dec. 2020-Aug. 2021," Morbidity and Mortality Weekly Report (MMWR), vol. 70, No. 34, pp. 1167-1169, (Aug. 27, 2021). DOI: http://dx.doi.org/10.15585/mmwr.mm7034e4.

CDC Seasonal Flu Vaccine Effectiveness Studies, Content source: Centers for Disease Control and Prevention, National Center for Immunization and Respiratory Diseases (NCIRD); Page last reviewed: Aug. 26, 2021.

"Measles, Mumps, and Rubella (MMR) Vaccination: What Everyone Should Know," National Center for Immunization and Respiratory Diseases; Page last reviewed: Jan. 26, 2021.

"Adjuvants and Vaccines," Centers for Disease Control and Prevention, National Center for Emerging and Zoonotic Infectious Diseases (NCEZID), Division of Healthcare; Page last reviewed: Aug. 14, 2020.

De Andrea, M. et al, "The Interferon System: An Overview," European Journal of Paediatric Neurology, vol. 6, suppl. A, A41-A46, (2002). DOI: 10.1053/ejpn.2002.0573.

Parkin, J. et al, "An Overview of the Immune System," Lancet, vol. 357, pp. 1777-1789 (Jun. 2, 2001).

Ishikawa, H. et al, "STING an Endoplasmic Reticulum Adaptor that Facilitates Innate Immune Signaling," Nature, vol. 455, No. 7213, pp. 674-678 (Oct. 2, 2008). DOI:10.1038/nature07317.

Motani, K. et al., "Activation of Stimulator of Interferon Genes (STING) Induces ADAM17-mediated Shedding of the Immune Semaphorin SEMA4D," J. Biol. Chem., vol. 293, No. 20, pp. 7717-7726, 2018; doi.10.1074/jbc.RA118.002175.

Ishikawa, H. et al, "STING Regulates Intracellular DNA-mediated, Type 1, Interfereon-dependent Innate Immunity." Nature, vol. 461, No. 7265, pp. 788-792 (Oct. 8, 2009). DOI:10.1038/nature08476.

Schoggins, J.W., "Interferon Signaling: What is an Interferon-Stimulated Gene?" Annual Review of Virology, vol. 6, pp. 567-584 (2019).

Sa Ribero, M. et al, "Interplay Between SARS-CoV-2 and the Type I Interferon Response," PLOS Pathogens, vol. 16, No. 7, 22 pgs., (Jul. 29, 2020). https://doi.org/10.1371/journal.ppat.1008737.

Sun, W. et al., "ERIS, an Endoplasmic Reticulum IFN Stimulator, Activates Innate Immune Signaling Through Dimerization," PNAS, vol. 106, No. 21, pp. 8653-8658, (May 26, 2009). www.pnas.org/cgi/doi/10.1073/pnas.0900850106.

Abe, T. et al, "STING Recognition of Cytoplasmic DNA Instigates Cellular Defense," Molecular Cell, vol. 50 (1), 5-15, (Apr. 11, 2013). http://dx.doi.org/10.1016/j.molcel.2013.01.039.

Barber, G.N, "STING: Infection, Inflammation and Cancer," Nature, vol. 15, No. 12, pp. 760-770, (Dec. 2015). doi:10.1038/nri3921.

Ramanjulu, J.M. et al, "Design of Amidobenzimidazole STING Receptor Agonists with Systemic Activity," Nature, vol. 564, pp. 439-443 (Dec. 20/27, 2018). https://doi.org/10.1038/s41586-018-0705-y.

Sali, T.M. et al, "Characterization of a Novel Human-Specific STING Agonist that Elicits Antiviral Activity Against Emerging Alphaviruses," PLOS Pathogens, pp. 1-30, (Dec. 8, 2015). DOI:10.1371/journal.ppat.1005324.

Guo, F. et al, "STING Agonists Induce an Innate Antiviral Immune Response against Hepatitis B Virus," Antimicrobial Agents and Chemotherapy, vol. 59, No. 2, pp. 1273-1281, (Feb. 2015). http://dx.doi.org/10.1128/AAC.04321-14.

Conlon, J. et al, "Mouse, but not Human STING, Binds and Signals in Response to the Vascular Disrupting Agent 5,6-Dimethylxanthenone-4-Acetic Acid," Journal of Immunology, (2013). 190:5216-5225; doi: 10.4049/jimmunol.1300097.

Liu, S. et al, "STING Signaling Promotes Apoptosis, Necrosis, and Cell Death: An Overview and Update," Mediators of Inflammation, (vol. 2018), Article ID 1202797, 4 pages; https://doi.org/10.1155/2018/1202797.

Zhu, Y. et al., "STING: A Master Regulator in the Cancer-Immunity Cycle," Molecular Cancer, vol. 18:152, (2019). https://doi.org/10.1186/s12943-019-1087-y.

Simon, A.K. et al, "Evolution of the Immune System in Humans from Infancy to Old Age," Proc. R. Soc. B 282:20143085; (2015). http://dx.doi.org/10.1098/rspb.2014.3085.

Thompson, J.F. et al,"Chemoablation of Metastatic Melanoma Using Intralesional Rose Bengal," Melanoma Research, vol. 18, (2008) pp. 405-411.

Swift, L. et al, "In Vitro and Xenograft Anti-Tumor Activity, Target Modulation and Drug Synergy Studies of PV-10 Against Refractory Pediatric Solid Tumors," Abstract 10557, 2018 ASCO Annual Meeting I, Journal of Clinical Oncology, 36.15, (2018). DOI: 10.1200/JCO.

Swift, L. et al., "Potent in vitro and Xenograft Antitumor Activity of a Novel Agent, PV-10, Against Relapsed and Refractory Neuroblastoma," OncoTargets and Therapy, vol. 12, pp. 1293-1307, (2019).

"A Unique Approach that Helps Close the Clinical Gap in Protection," Dynavax Technologies Corporation (2021).

Kawai, T. et al, "TLR Signaling," Cell Death and Differentiation, vol. 13, pp. 816-825, (2006).

O'Neill, L.A.J. et al., "Therapeutic Targeting of Toll-Like Receptors for Infectious and Inflammatory Diseases and Cancer," Pharmacological Reviews, vol. 61, No. 2, pp. 177-197 (2009).

Yiu, H. et al, "Dynamics of a Cytokine Storm," PLoS One, vol. 7,No. 10: e45027 (Oct. 1, 2012). doi:10.1371/journal.pone.0045027.

Rowaiye, A.B. et al, "Attenuating the Effects of Novel COVID-19 (SARS-CoV-2) Infection-Induced Cytokine Storm and the Implications," Journal of Inflammation Research, vol. 14, pp. 1487-1510 (2021). http://doi.org/10.2147/JIR.S301784.

Tisoncik, J.R. et al, "Into the Eye of the Cytokine Storm," Microbiology and Molecular Biology Reviews, vol. 76, No. 1, pp. 16-32 (Mar. 2012).

Diorio, C. et al, "Multisystem Inflammatory Syndrome in Children and COVID-19 are Distinct Presentations of SARS-CoV-2," The Journal of Clinical Investigation, vol. 130, No. 11, pp. 5967-5975 (Nov. 2020). https://doi.org/10.1172/JCI140970.

Lee, D.W. et al, "Current Concepts in the Diagnosis and Management of Cytokine Release Syndrome," Blood, vol. 124, No. 2, pp. 188-195, (Jul. 10, 2014). DOI 10.1182/blood-2014-05-552729.

Liu, H. et al, "Intralesional Rose Bengal in Melanoma Elicits Tumor Immunity via Activation of Dendritic Cells by the Release of High Mobility Group Box 1," Oncotarget, vol. 7, No. 25, pp. 37893-37905; (May 9, 2016).

Krueger, J.G. et al, "P013 Immune Modulation by Topical PH-10 Aqueous Hydrogel (rose Bengal disodium) in Psoriasis Lesions," Psoriasis from gene to clinic, Programme & Abstracts Nov. 30-Dec. 2, 2017 p. 79, 8th International Congress, The Queen Elizabeth II Conference Centre, London, UK Nov. 30-Dec. 2, 2017 (2018).

Tsao, S. et al, "Protein-Mediated Hepatic Uptake of Rose Bengal in Analbuminemic Mutant Rats (NAR)," Drug Metabolism and Disposition, vol. 16, No. 3, pp. 482-489, (1988). 0090-9556/88/1603-0482S02.00/0.

(56) References Cited

OTHER PUBLICATIONS

Meurman, L., "Acta Medica Scan," Supp 167, Chapters I, III, V, VII, X and XII (1960).
Green, F.J., Sigma-Aldrich Handbook of Stains, Dyes and Indicators, Aldrich Chemical Company, Inc., Milwaukee, WI, pp. 637-638 (1990).
Delprat, G.D. et al, "A New Liver Function Test: The Elimination of Rose Bengal When Injected Into the Circulation of Human Subjects," Achives of Internal Medicine, vol. 34, pp. 533-541, (1924).
Taplin, G.V. et al, "Radioactive Rose Bengal Uptake-Excretion Test," The Journal of Laboratory and Clinical Medicine, vol. 45, No. 5, pp. 665-678, (1955).
Yoshimoto, M. et al, "Effects of Coal Tar Dyes on Viability, and RNA and Protein Syntheses in Isolated Rat Hepatocytes," J. Food Hyg. Soc. Japan vol. 25, No. 4, pp. 347-351, (Aug. 1984).
Berge, S.M. et al., "Pharmaceutical Salts," Journal of Pharmaceutical Sciences, vol. 66, No. 1, pp. 1-19 (1977).
Swift, L. et al, "In Vitro Activity and Target Modulation of PV-10 Against Relapsed and Refractory Pediatric Leukemia," Blood, 132 (Supplement 1): 5207 (2018). https://doi.org/10.1182/blood-2018-99-119438.
Clapp, T. et al, "Vaccines with Aluminum-Containing Adjuvants: Optimizing Vaccine Efficacy and Thermal Stability," J Pharm Sci, vol. 100, No. 2, pp. 388-401 (Feb. 2011). doi:10.1002/jps.22284.
Shardlow, E. et al, "Unraveling the Enigma: Elucidating the Relationship Between the Physicochemical Properties of Aluminium-Based Adjuvants and Their Immunological Mechanisms of Action," Allergy, Asthma & Clinical Immunology, 14:80, pp. 2-18 (2018). https://doi.org/10.1186/s13223-018-0305-2.
Wachter, E. et al, "Functional Imaging of Photosensitizers using Multiphoton Microscopy," Multiphoton Microscopy in the Biomedical Sciences II, SPIE Paper 4620-29, pp. 143-147, BiOS 2002 (Biomedical Optics), San Jose, CA (Jan. 21, 2002).
Ge, Z. et al, "TIGIT, the Next Step Towards Successful Combination Immune Checkpoint Therapy in Cancer," Front. Immunol, vol. 12, pp. 1-13, (Jul. 2021). https://www.frontiersin.org/journals/immunology#articles.
Thompson, J.F. et al, "Chemoablation of Metastatic Melanoma Using Intralesional Rose Bengal," Melanoma Research, vol. 18, pp. 405-411 (2008).
Graham, B.S. et al, "Structure-Based Vaccine Antigen Design," Annu Rev Med., vol. 70, pp. 91-104, Jan. 27, 2019. doi:10.1146/annurev-med-121217-094234.
Wrapp, D. et al, "Cryo-EM Structure of the 2019-nCoV Spike in the Profusion Conformation," Science, vol. 367, pp. 1260-1263, (Mar. 13, 2020).
Dou, Y. et al,"HBV-Derived Synthetic Long Peptide Can Boost CD4+ and CD8+ T-Cell Responses in Chronic HBV Patients Ex Vivo," The Journal of Infectious Diseases, vol. 217, pp. 827-839 (Mar. 1, 2018).
Rauf et al., *Spectrochim Acta* Part A 72 133-137 (2009).
Pan et al., *J Immunol* 7(8):e44142 (Aug. 30, 2012).
Conlon et al., *J Immunol* 190(10):5216-5225 (May 15, 2013).
Hwang et al., *Org Biomol Chem* 17:1869-1874 (2019).
Gao et al., *Cell Reports* 8:1668-1676 (Sep. 25, 2014).
Motedayen et al. *J. Clin. Med.* 9 3323 (Oct. 16, 2020).
Kim et al., *ACS Chem Biol.* 8(7): 1396-1401 (Jul. 19, 2013).
*Oxford Dictionary of Biochemistry and Molecular Biology*, Oxford University Press, Inc., New York, pp. 18 & 326 (1997).
*The American Heritage Stedman's Medical Dictionary*, Houghton Mifflin Co., Boston, p. 19 (2002).
W. Levinson, *Review of Medical Microbiology and Immunology*, 14th ed., McGraw-Hill Education, Chicago, pp. 498 & 535 (2016).
A. Abbas et al., *Basic Immunology*, 5th ed., Elsevier, St. Louis, pp. 276 & 287-288 (2016).
E. Liddell, in *The Immunoassay Handbook*, 4th ed., D. Wilder ed., "Antibodies", Elsevier Science, Amsterdam, NL, (2013).
G. Kaiser, *LibreTexts*, UC Davis, p. 12.2:Antigens and Epitopes, 12.2.1-12.2.3, https://bio.libretexts.org/@go/page/3292?pdf (Apr. 9, 2022).
Office Action re Japanese application No. JP 2022-558585, dated Dec. 12, 2023.

\* cited by examiner

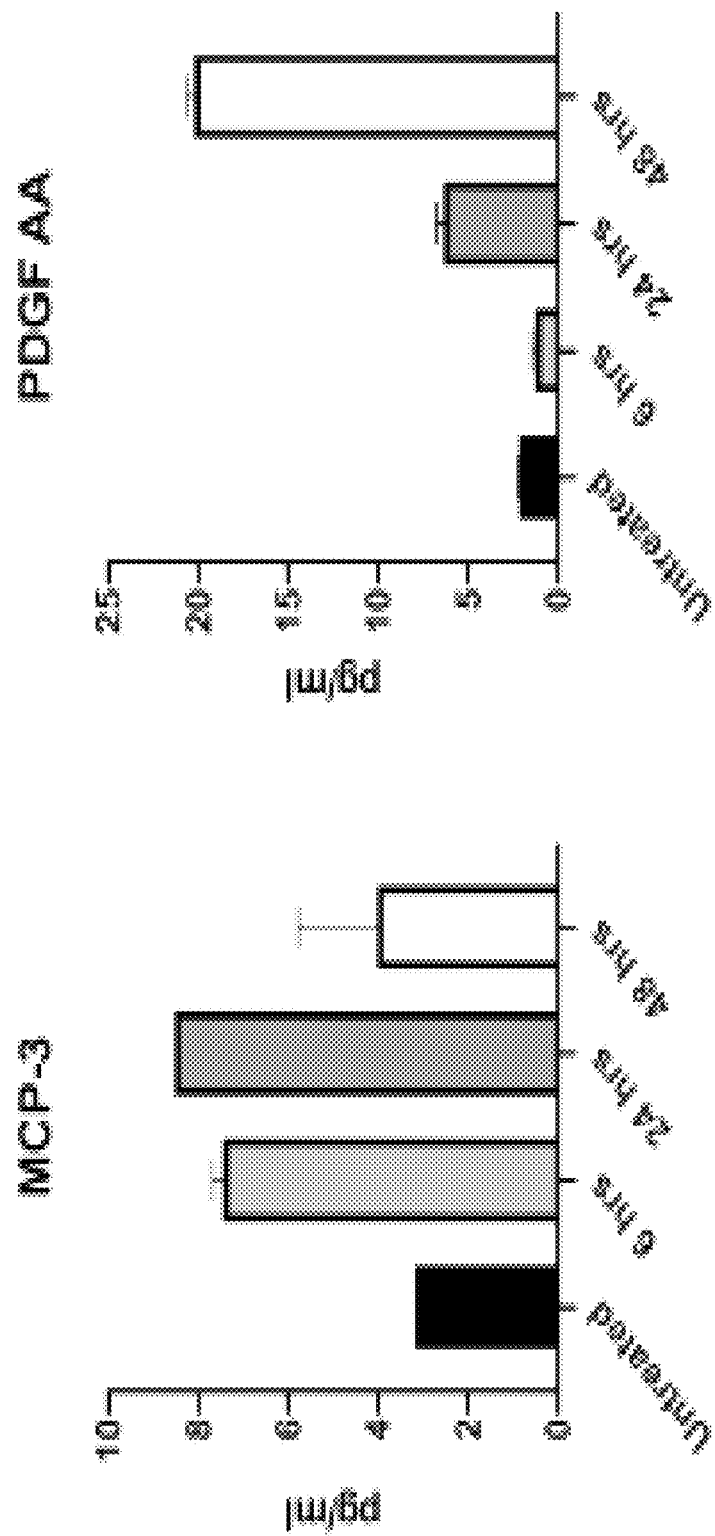

HALOGENATED XANTHENES AS VACCINE ADJUVANTS

CROSS-REFERENCE TO RELATED APPLICATION

This is a continuation-in-part of application Ser. No. 17/212,723 filed on Mar. 25, 2021, that claimed priority from application No. 63/000,231, filed on Mar. 26, 2020.

BACKGROUND ART

The human immune system is composed of two components, the innate and the adaptive immune systems. The innate immune system is encoded in the germline of an organism and constitutes the first line of defense in mammals, responding to pathogens and abnormal cells through the initiation of intracellular signaling cascades that lead to the activation of transcription factors that trigger the production of cytokines and chemokines with the participation of multiple cell types, including dendritic cells (DCs), macrophages, neutrophils, and natural killer cells [Beutler, *Mol. Immunol.* 2004, 40:845-859].

The subsequent adaptive immune system is acquired and involves antigen-specific T cell and B cell responses mediated by immunogen-presenting DCs. The adaptive immune system serves to provide longer term protection to the host through the action of T cell receptors and antibodies that neutralize the pathogens and abnormal cells [Beutler, *Mol. Immunol.* 2004, 40:845-859; and Hoebe et al., *Nat. Immunol.* 2004, 5:971-974].

Oncology and virology are tangentially related fields that intersect at the innate and adaptive immune systems of mammals, in particular humans. Whereas disease etiology and manifestations are generally distinct, this intersection provides a common basis for the application of discoveries in one field to the other. Here, we synthesize novel approaches applicable to both fields by fusing new discoveries independently made in each field to provide new adjuvants for vaccines.

Current Vaccine Shortcomings

Recent advances in vaccine discovery and preparation have marvelously been able to be developed in a record short period of time to successfully battle the severe acute respiratory syndrome coronavirus 2 (SARS-CoV-2) virus and the disease it causes, coronavirus disease 2019 (COVID-19) disease. The recently isolated SARS-CoV-2 Delta variant appears to be more virulent, but still generally preventable with the vaccines that we now have available.

The Centers for Disease Control and Prevention (CDC) *Morbidity and Mortality Weekly Report (MMWR)*/Aug. 27, 2021/70(34):1167-1169 noted that for 2,875 fully vaccinated persons over 329,865 person days pre-Delta variant, adjusted vaccine effectiveness was calculated to be 91 percent, with 10 persons becoming ill with SARS-CoV-2 infection. In the time of Delta variant predominance, among 2,352 fully vaccinated persons over 119,218 person days, adjusted vaccine effectiveness was calculated as 66 percent, with 24 persons becoming ill with SARS-CoV-2 infection. Vaccine origins were not segregated in the above report report.

Even though only 10 of 2,875 fully vaccinated persons became ill with SARS-CoV-2 infection prior to the predominance of the Delta variant, that percentage of diseases (about 0.3 percent) would translate to about 0.999 million cases if the whole United States (U.S.) population (about 333 million people) were vaccinated. Using the numbers from the post-Delta variant prevalence from the above article [(24/2352)×333,000,000], the number of cases would be about 3.4 million.

For vaccinations against hepatitis B, the CDC estimates that over 90 percent of individuals will develop antibodies. [CDC, *Viral Hepatitis—Hepatitis B FAQs for the Public—Is the Hepatitis B Series Effective*? May 23, 2016.] The CDC reports that vaccines against seasonal flu (influenza A) have been between 10 and 60 percent effective in the seasons of 2004-2005 through 2019-2020. [*CDC Seasonal Flu Vaccine Effectiveness Studies*; Centers for Disease Control and Prevention, National Center for Immunization and Respiratory Diseases (NCIRD), last reviewed Aug. 26, 2021.]

Results for the tripartite measles-mumps-rubella (MMR) vaccine are similar. The CDC reports that one dose of MMR vaccine is 93 percent effective against measles, 78 percent effective against mumps, and 97 percent effective against rubella. Two doses of MMR vaccine are 97 percent effective against measles and 88 percent effective against mumps, with no report rubella after two doses. [*Measles, Mumps, and Rubella (MMR) Vaccination: What Everyone Should Know*; National Center for Immunization and Respiratory Diseases; last reviewed Jan. 26, 2021.]

It is thus seen that although many modern vaccines are effective for most of the population, they all miss some recipients for whom they are not effective, even those that have been vaccinated against the particular disease. Life-saving improvements to vaccines therefore need to be made.

The usually-used hepatitis B vaccines contain an aluminum-containing adjuvant. One U.S. Food and Drug Administration (FDA)-approved hepatitis B vaccine uses a proprietary adjuvant to improve its efficacy. That vaccine is sold under the tradename Heplisav-B® and includes an adjuvant called CpG 1018. CPG 1018 is said to be a 22-mer phosphorothioate-linked oligonucleotide that targets TLR9 and is said to cause increased antibody concentration, stimulates helper (CD4+) and cytotoxic (CD8+) T cell populations, and generates robust T and B cell memory responses.

Adjuvants help create a stronger immune response in people receiving a vaccine. Several adjuvants approved by the U.S. FDA contain aluminum salts such as amorphous aluminum hydroxyphosphate sulfate (AAHS), aluminum hydroxide, aluminum phosphate, and potassium aluminum sulfate (Alum). A monophosphoryl lipid A (MPL) formerly sold as AS04 but not presently used in the United States, and another MPL called $AS01_B$, are isolated from the surface of bacteria. $AS01_B$ also includes QS-21, a natural compound extracted from the Chilean soapbark tree (*Quillaja saponaria molina*). The final presently U.S. FDA-approved adjuvant is an oil-in-water emulsion composed of squalene and is named a MF59. [*Adjuvants and Vaccines*, Centers for Disease Control and Prevention, National Center for Emerging and Zoonotic Infectious Diseases (NCEZID), Division of Healthcare Quality Promotion (DHQP); Last reviewed Aug. 14, 2020.]

Inflammatory Reactions to Viral Infection

Rampant viral infection of tropic host cells can elicit severe local or systemic inflammatory reactions due to release of inflammatory signaling components from infected cells (e.g., cytokines, chemokines, and damage-associated molecular patterns [DAMPs] implicated in innate immune response; and T cells and other functional components of an adaptive immune response), leading to local or systemic symptoms of the infection. Approaches that treat such disease manifestations, such as reducing severe pulmonary inflammatory response, can provide vital disease control until the patient can mount an appropriate anti-viral response, either through anti-viral drug therapy and/or an adaptive immune response.

Although there are several agents that may have merit for controlling viral disease, through prevention of viral infection of tropic cells or functional activity of virus within infected tropic cells, or through modulation of uncontrolled inflammatory response during viral infection, new options for anti-viral agents are clearly needed.

Interferon

Interferons (IFNs) are a class of signaling proteins (i.e., cytokines) central to cellular defense against viruses, infectious microbes and tumor cells. [Andrea et al., *Eur J Paed Neurol* 6 Suppl A (6):A41-A46 (2002).] For example, a virus-infected host cell releases IFNs, signaling nearby cells to heighten their antiviral defenses. Interferons were named for their ability to "interfere" with viral replication by protecting cells from virus infections. [Parkin et al., *Lancet* 357 (9270):1777-1789 (2001).]

In addition to direct antiviral effects, IFNs serve to activate immune cells (e.g., natural killer cells and macrophages) and up-regulate antigen presentation by increasing expression of major histocompatibility complex (MHC) antigens. IFNs are classified into three groups:

Type I IFN, consisting of IFN-α, IFN-β, IFN-ε, IFN-κ, and IFN-ω, are produced in response to viruses and, upon binding to cellular receptors, inhibit replication of viral RNA and DNA; Type I IFN has an analogous role in immune signaling in response to cancer;

Type II IFN (IFN-γ) is activated by interleukin-12 (IL-12) and released by cytotoxic T cells and T helper cells; and Type III IFN is implicated in immune responses to some types of viral and fungal infections.

STING Activation and Immune Activation

The stimulator of interferon genes (STING), a transmembrane protein resident in the endoplasmic reticulum (ER), is an important regulator of innate immunity and was first reported by Ishikawa et al., *Nature* 455(7213):674-678 (2008). Those authors found that STING induces a Type I IFN response and exerts a potent antiviral state upon expression, whereas loss of STING can render cells extremely susceptible to viral infection.

More specifically, STING is usually activated by binding to cyclic di-nucleotides such as cGMP-AMP (cGAMP), which is produced as an intracellular second messenger when cGAMP synthase recognizes cytosolic DNA.

Binding to cGAMP causes STING to dimerize and translocate from the ER to the Golgi apparatus. After relocation, STING recruits a serine/threonine kinase, TANK binding kinase 1 (TBK1), leading to the phosphorylation of interferon regulatory factor 3 [IRF3] and the up-regulation of Type I IFN and IFN-stimulated genes, including IFN-β and CXCL10. [Motani et al., *J Biol Chem* 293(20):7717-7726 (2018).]

Ishikawa et al., *Nature* 461(8):788-793 (2009) showed that STING deficiency in mice produces lethal susceptibility to herpes simplex virus type 1 (HSV-1) infection due to the lack of a successful Type I IFN response.

STING induces Type I IFN production when cells are infected with intracellular pathogens, which protects infected cells and nearby cells from local infection by binding to the same cell that secretes it (i.e., autocrine signaling) and nearby cells (i.e., paracrine signaling). A Type I interferon (IFN-I) response can be critical for providing an efficient protection against viral infections.

IFN-I production is rapidly triggered by the recognition by host sensors of pathogen-associated molecular patterns (PAMPs), such as viral nucleic acids. IFN-I-induced signaling converges on transcription factors, which rapidly induces the expression of hundreds of genes called interferon-stimulated genes (ISGs) [reviewed in Schoggins, *Annu Rev Virol.* 6(1):567-584 (2019)]. This antiviral signaling cascade occurs in virtually all cell types exposed to IFN-I.

ISGs, along with other downstream molecules controlled by IFN-I (including pro-inflammatory cytokines), have diverse functions, ranging from direct inhibition of viral replication to the recruitment and activation of various immune cells. A robust, well-timed, and localized IFN-I response is thus usually needed as a first line of defense against viral infection because it promotes virus clearance, induces tissue repair, and triggers a prolonged adaptive immune response against viruses. Sa Ribero et al., *Plos Pathog* 16(7):e1008737 (Jul. 29, 2020).

Sun et al., *Proc Natl Acad Sci, USA*, 105(21):8653-8658 (2009) showed that dimerization of STING was critical to this innate immune system signaling. Abe et al., *Mol Cell* 50:5-15 (2013) showed that acute STING activation (via dimerization) was required for protective function, whereas chronic activation can lead to counterproductive inflammatory response and autoimmune disease.

In some cases, STING acts as an intracellular sensor of foreign and endogenous DNA, such as that leaked from a host cell nucleus and infecting pathogens. Such endogenous DNA may be responsible for autoinflammatory diseases, such as systemic lupus erythematosus (SLE) or Aicardi-Goutières syndrome (AGS). [Barber, *Nat Rev Immunol* 15(12):760-770 (December 2015).] Interestingly, it appears that, as described by Abe et al., above, regarding antiviral activity, acute STING activation (via dimerization) is required for protective function, whereas chronic activation can lead to immune down-regulation.

Barber, above, notes similar activity against retroviruses and replication of RNA viruses. Thus, expression and dimerization of STING play critical cellular defense roles against infection from all major viral classes.

In addition to its antiviral role, Barber, above, also describes a similar function against bacterial infection. In that review, Barber noted that their studies highlight the delicate equilibrium between an appropriate immune response and inflammation, a balance that may be exploited by microorganisms. Barber further noted that those findings may have important implications in the development of STING-targeting adjuvants and the design of vaccines intended to induce robust, long-lasting, adaptive immune responses.

These observations indicate that acute activation of STING can be crucial for anti-microbial activity (i.e., antiviral, anti-bacterial, anti-fungal, or anti-parasitic).

Recent research has shown that STING homodimers complex with cytoplasmic polynucleotides, particularly viral-related single-stranded and double-stranded DNA (ssDNA and dsDNA) molecules. Such dimeric STING-containing complexes were found indispensable for HSV-1-mediated transcriptional activation of a wide array of innate immune and pro-inflammatory genes in addition to Type I IFN. [Abe et al., *Mol Cell* 50:5-15 (2013).]

STING activation in certain cell types triggers cell death, including apoptosis and necrosis. This effect could be critical for preventing unnecessary or excessive inflammatory events and maintaining host immune homeostasis. Besides canonical immune responses represented by Type I IFN and tumor necrosis factor (TNF) production, STING signaling can also induce cell death events in a variety of cell types.

Currently, several STING agonists have been developed to treat refractory malignancies. See, for example, the use of linked amidobenzimidazole (ABZI)-based compounds in Ramanjulu et al., *Nature* 564:439-443 (December 20/27 2018).

Sali et al., (*PLoS Pathog*, pages 1-30, Dec. 8, 2015) reported identification of a small molecule STING agonist capable of activating the Type I IFN response by way of the transcription factor IFN regulatory factor 3 (IRF3). That small molecule, also referred to as G10, whose structural formula is shown below, triggered IRF3/IFN-associated transcription in human fibroblasts.

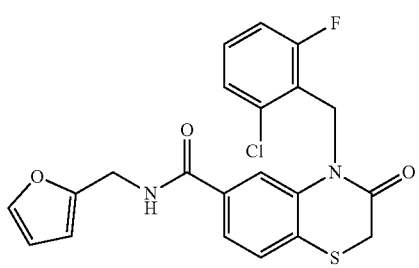

G10

Further examination of the cellular response to that molecule revealed expression of multiple IRF3-dependent antiviral effector genes as well as Type I and Type III IFN subtypes. This led to the establishment of a cellular state that prevented replication of emerging ssRNA alphavirus species including Chikungunya virus, Venezuelan Equine Encephalitis virus, and Sindbis virus. Those authors reported that the G10 molecule did not bind directly to STING, but acted as an indirect activator of human STING-dependent phenotypes.

Guo et al., [*Antimicrob Agents Chemother* 59(2):1273-1281 (2015)] reported that the synthetic small molecule, 5,6-dimethylxanthenone-4-acetic acid (DMXAA) and whose structure is shown below, activated a

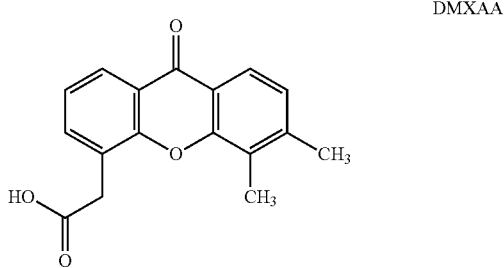 [SMILES: Cc1ccc2c(=O)c3cccc(CC(=O)O)c3oc2c1C]

DMXAA

STING-dependent signaling pathway to induce a Type I IFN-dominant cytokine response in mouse macrophages, which efficiently suppressed HBV replication in cultured murine hepatocytes and in the livers of mice by reducing the amount of cytoplasmic viral nucleocapsids. DMXAA had previously been identified as an agonist for murine STING. Human STING failed to bind to or signal in response to DMXAA. [Conlon et al., *J Immunol* 190:5216-5225 (2013).] The direct effect of STING in this cascade appears to be on DCs, which serve as intermediaries between the innate and adaptive immune systems.

STING has been recognized as an activator of immune responses by TBK1/IRF3 and NF-κB pathways and subsequent IFN and TNF production. STING is suggested to play critical roles in host defense, autoimmune diseases, and tumor immunity through the induction of pro-inflammatory cytokines. The application of targeting the STING pathway for cancer immunotherapy has been also been examined. [Liu et al., *Mediat Inflamm* (2018) Article ID 1202797, (4 pages).]

Zhu et al., *Mol Cancer* 18:152 (2019) reviewed the activity of STING in cancer treatments. They report that numerous studies have shown that the activation of STING and the stimulation of Type I IFN production are critical for the anti-cancer immune response.

Zhu et al. note that emerging evidence suggests that STING also regulates anti-cancer immunity in a Type I IFN-independent manner. For instance, STING has been shown to induce cell death and facilitate the release of cancer cell antigens. Moreover, STING activation has been demonstrated to enhance cancer antigen presentation, contribute to the priming and activation of T cells, facilitate the trafficking and infiltration of T cells into tumors, and promote the recognition and killing of cancer cells by T cells.

Those authors also report that many studies also revealed that Type I IFNs contribute to the control of tumors both in vivo and in vitro. These studies suggest that Type I IFNs play central roles in the anti-tumor response. However, recent studies have suggested that Type I IFNs may also impair anti-cancer immunity and even cause unexpected treatment failure for cancer. For example, IFN-β has been shown to induce the production of programmed cell death ligand 1 (PD-L1) and programmed cell death ligand 2 (PD-L2) in tumor cells, which can contribute to immune escape by cancer cells.

Barber [*Nat Rev Immunol* 15(12):760-770 (December 2015)] reviewed the role of STING-dependent innate immune signaling that largely parallels that in virology. STING activation leads to activation of Type I IFN, which has a priming effect on the adaptive immune system (activation of tumor antigen-specific T cells though cross-presentation of tumor antigens by DCs). Abrogation of STING in mice abrogates T cell response to melanoma as well as the activity of immune checkpoint inhibitors, and, as observed in virology, Barber notes that chronic STING activation can play a role in promoting tumorigenesis.

Barber concluded by noting "it is becoming apparent that STING has a key role in facilitating anti-tumour immune responses. Furthermore, stimulating STING activity within the tumour microenvironment may comprise a new immunotherapeutic strategy to help treat malignant disease." [Barber, *Nat Rev Immunol* 15(12):768 (2015)]

Immune function increases rapidly during early childhood and remains consistent across adulthood until onset of advanced age, as described by Simon et al., *Proc R Soc B* 282:20143085 (2015). Those authors note that the immune system undergoes profound remodeling and decline as a person ages. This immune senescence predisposes older adults to higher risk of acute viral and bacterial infection.

Although there appear to be little direct data on changes in STING expression and activation over age, it is likely that this tracks the same pattern of overall decline in innate immunity with onset of advanced age (i.e., 60 years or greater), especially given the central role of STING in mediating innate anti-viral immunity. These authors note a parallel increase in incidence of cancers with age (i.e., median age of onset of approximately 70 years in industrialized countries) that may also be attributable to the decline of STING expression and activation with increasing age.

Further, the consistent observations of productive outcome for acute STING activation and counterproductive outcome for chronic STING activation in infectious disease and oncology point to a central role for acute STING activation in the treatment of both infectious diseases and oncology indications.

The present invention illustrates the links between antimicrobial and anti-cancer activities as a new adjuvant for improving a vaccine-based treatment for both microbial infection and cancerous growth using a halogenated xanthene such as rose bengal as an adjuvant additive to a vaccine of choice.

BRIEF SUMMARY OF THE INVENTION

The present invention contemplates the medicinal use of a halogenated xanthene (HX) compound as an adjuvant to an immunogen in a vaccine for administration to mammals, such as humans. A contemplated halogenated xanthene (HX) compound can be used by itself or as its pharmaceutically acceptable salts, an amide whose nitrogen atom is unsubstituted, substituted with one or two $C_1$-$C_4$ alkyl groups that are the same or different or together with the amido nitrogen atom form a 5- or 6-membered ring, a $C_1$-$C_4$ alkyl ester, or an aromatic derivative (amide or ester) thereof. The aromatic derivative is an ester or amide formed from an alcohol or monosubstituted amine having a 5- or 6-membered aromatic ring, or a 5,6- or 6,6-fused aromatic ring system that contains 0, 1 or 2 hetero ring atoms that are independently nitrogen, oxygen or sulfur. Rose bengal is a preferred HX compound and its disodium salt, rose bengal disodium, is the most preferred HX compound.

One embodiment of the invention contemplates a vaccine composition that contains an immunogen present in a vaccine-effective amount dissolved or dispersed in a pharmaceutically acceptable diluent such as water or 0.9% saline, along with an adjuvant-effective amount of a halogenated xanthene as discussed above. An adjuvant-effective amount of the halogenated xanthene compound (HX) is an amount that is less than a cytotoxic amount as would be used to kill cancerous cells, for example, but an amount sufficient to cause STING dimerization.

Another contemplated embodiment is a vessel or a container, such as a vial, bottle or other suitable means, holding a concentrated pre-vaccine composition that contains an immunogen and the HX compound discussed above. The amounts of the two components are predetermined to provide a vaccine-effective amount and an adjuvant-effective amount of the immunogen and HX compound, respectively, to provide a vaccine on dissolution or dispersion in a predetermined amount of a pharmaceutically acceptable diluent when the vaccine is prepared.

A mammalian HX compound-adjuvanted vaccine composition and a corresponding concentrated pre-vaccine composition can also contain one or more excipients. Illustrative excipients include buffer salts, osmotic agents to provide a desired osmolarity or osmolality to the composition, and one or more additional adjuvants. Illustrative, preferred additional adjuvants include one or more usually-used aluminum-containing vaccine adjuvant, as well as one or more so-called "check point inhibitors" that are typically monoclonal antibodies that help stimulate the production of T cells such as CD4 and CD8 T cells. Such excipients, as are customary in vaccine-related pharmacy, can be present in amounts of about 0.001% by weight to 10% by weight of a mammalian HX compound-adjuvanted vaccine composition, preferably 0.1 to 10% by weight, based weight of the vaccine composition. Excipients are discussed in greater detail hereinafter.

A further embodiment of the invention is an improved vaccine composition that contains a vaccine-effective amount of a predetermined immunogen dissolved or dispersed in a pharmaceutically acceptable diluent in which the improvement comprises an adjuvant-effective amount of a halogenated xanthene (HX) compound as discussed above that is also dissolved or dispersed with the immunogen in that pharmaceutically acceptable diluent.

The articles "a" and "an" are used herein to refer to one or more than one (i.e., to at least one) of the grammatical object of the article. By way of example, "an element" means one element or more than one element.

Each of the patents, patent applications, and articles cited herein is incorporated by reference.

BRIEF DESCRIPTION OF THE DRAWINGS

In the drawings forming a portion of this disclosure

FIG. 1B utilized a longer film exposure than FIG. 1A to highlight the presence of the STING dimer.

In FIGS. 3, 4, and 5, "NP" means "no peptide"; Pep 1 is the peptide "ATVELLSFLPSDFFPSV (HLA-A*02)" of SEQ ID NO: 1; Pep 2 is the peptide "FLPSDFFPSV (HLA-A*02)" of SEQ ID NO: 2; and Pep 3 is the peptide "LPSDFFPSV (HLA-B*51)" of SEQ ID NO: 3. PLC/PRF 5 is a human hepatoma cell line that expresses and secretes hepatitis B particles. "PV-10" is a sterile 10% solution of rose bengal (RB) in 0.9% saline, with the concentrations 5 µM, 10 µM, and 20 µM utilized in FIGS. 3-5 meaning the concentration of RB provided from the PV-10 solution utilized.

FIG. 4 is a series of bar graphs showing the number of IFN-gamma ELIspot images counted from CD8 cells cultured without the PLC/PRF 5 cells along with numbers for control cultures.

FIG. 5 shows photographic copies of ELIspot plates of CD8 cells co-cultured with DCs expressing one of the three hepatitis B virus (HBV) immunogenic peptides as noted along with the noted amounts of RB, but in the absence of PLC/PRF 5 cells.

DETAILED DESCRIPTION OF THE INVENTION

Figure 1A:
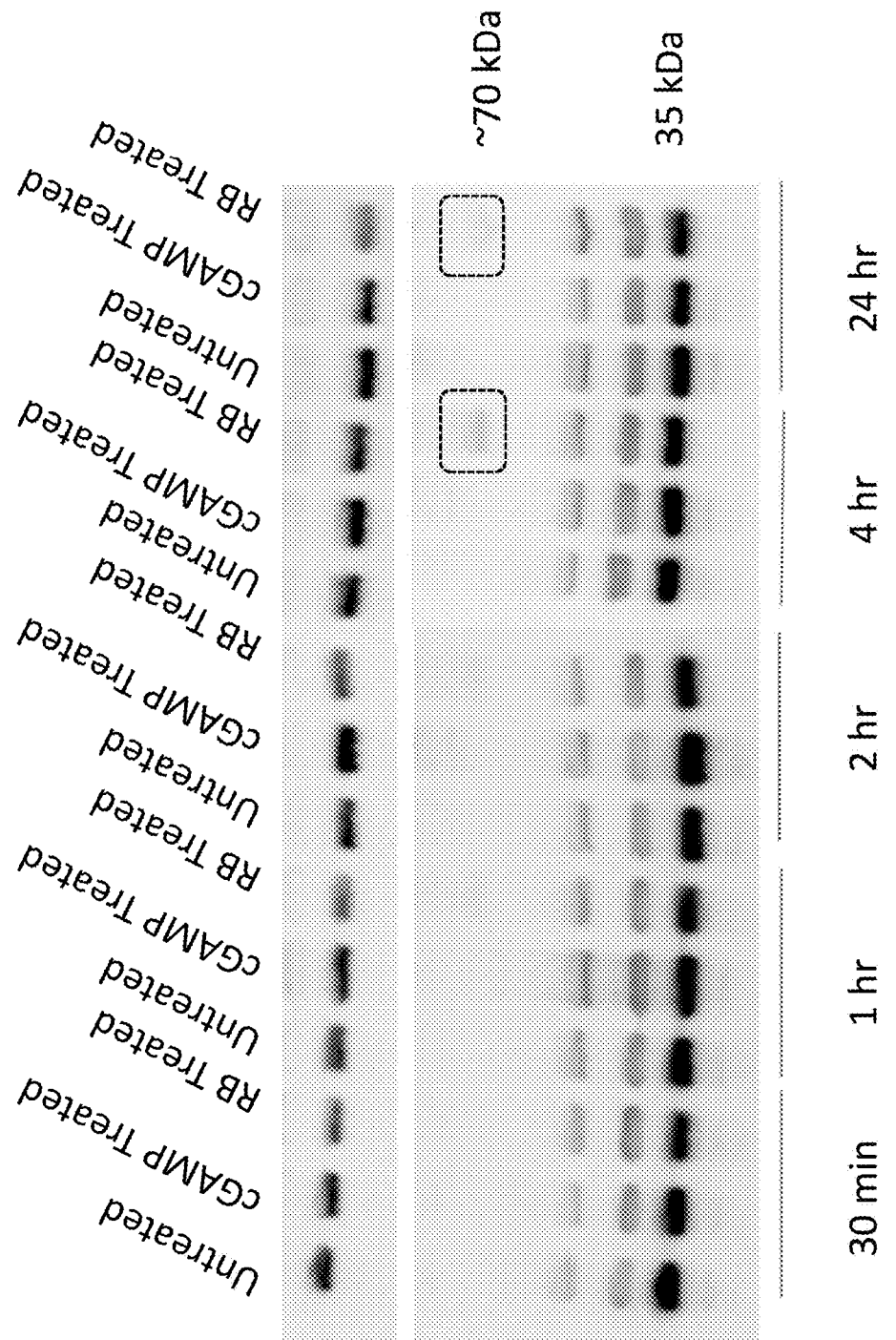
FIG. 1A and FIG. 1B are annotated photographs of Western blots from THP-1 acute monocytic leukemia (AML) cells contacted with rose bengal (RB) for 30 minutes and 1, 2, 4, and 24 hours, and for 2, 4, 6, and 8 hours, respectively, that led to the appearance of a new 70-KD STING dimer band (dotted boxes) detected by specific antibodies.

The present invention contemplates a vaccine and a method of enhancing a mammalian immunogen-specific immune response in a treated mammal. That method broadly comprises contacting mammalian cells present in a mammalian cell growth-supporting medium such as an in vitro culture plate or in vivo with a mammal's body, with an adjuvant-effective amount of a halogenated xanthene (HX) compound, a pharmaceutically acceptable salt, amide, ester, or aromatic derivative discussed previously, and an immunogen to which the immune response is to be enhanced.

The invention more particularly contemplates use of a halogenated xanthene (HX) compound, particularly rose bengal disodium, in a mammalian vaccine as an adjuvant that induces a Type I interferon (IFN) immune response from endogenously present STING, in conjunction with an immunogen when administered parenterally as by infusion in treating a cancerous tumor or a microbial infection. The two or more medicaments (adjuvant and immunogen) are preferably administered parenterally as by infusion from a single aqueous pharmaceutical composition such as normal saline. Separate aqueous pharmaceutical composition infusions can also be made, and are preferably carried out seriatim, or at most within about 4 hours of each other.

This immunogenic-response Type I IFN is different from those obtained by intralesional injection of RB or another HX compound into a tumor, or the contacting of malignant hematologic cells with RB as shown in U.S. Pat. Nos. 7,648,695, 8,557,298, 9,107,877, 10,130,658, 11,058,664, and the progeny of one or more thereof. The cancerous mammalian cells contacted in the above patents and application preferentially take up the RB, which kills the cancer cells and causes the resulting ablated cellular debris to act as a self-vaccine to induce a distant immune response. In this immunogenic response, the HX compound such as RB acts to stimulate the STING response, not to kill cells. Rose bengal disodium is the preferred HX compound.

Enhancement of the immune response can be determined by comparison of the appropriate immune molecules or cells such as cytokines, chemokines, antibodies, B cells and/or T cells by in vivo or in vitro techniques. Such comparisons can also be made by comparisons of tumor sizes, extent of viremia and the like that are usually utilized in this field.

In one more particular embodiment, the invention contemplates a mammalian vaccine composition that contains an immunogen present in a vaccine-effective amount dissolved or dispersed in a pharmaceutically acceptable diluent such as water or 0.9% saline, along with an adjuvant-effective amount of a halogenated xanthene (HX) compound as discussed above and in greater detail hereinafter. An adjuvant-effective amount of the halogenated xanthene compound (HX) is an amount that is less than a cytotoxic amount as would be used to kill cancerous cells, for example, but an amount sufficient to cause stimulator of interferon genes (STING) dimerization and concomitant induction of a Type I IFN immune response in the vaccinated mammal. This amount is also discussed further hereinafter. A contemplated vaccine can also include one or more excipients that are present at about 0.001% by weight to 10% by weight of a mammalian HX compound-adjuvanted vaccine composition. A mammalian vaccine composition containing an immunogen and a HX compound adjuvant as described in this paragraph is referred to hereinafter and in the claims as a mammalian HX compound-adjuvanted vaccine.

The present invention is contemplated to apply to any mammalian vaccine, particularly to a vaccine for humans. Preferably, the vaccine immunogen and possible additives with which the HX compound adjuvant is dissolved or dispersed is in liquid form when administered, and more preferably, that liquid is at least 80 percent by weight water.

There are six usually used classes (types or groups) of anti-microbial mammalian vaccines with which a HX compound adjuvant is formulated.

A first group is an "inactivated vaccine" that utilizes a killed version of the microbe as the immunogen. Illustrative examples include those that protect against hepatitis A, seasonal influenza A, the Salk polio vaccine and rabies vaccine. These vaccines are typically administered by injection (shot).

The next type utilizes a "live attenuated" microbe as the immunogen and include those that protect against measles, mumps, and rubella (MMT Combined vaccine), rotavirus, smallpox, chickenpox, and yellow fever. The Sabin orally administered polio vaccine is also a live-attenuated viral vaccine.

The third type is a "mRNA vaccine" that encodes one or more immunogenic microbial proteinaceous sequences as are the currently utilized COVID-19 vaccines (e.g., Moderna and Pfizer-BioNTech).

The fourth group are referred to as "subunit, recombinant construct such as the plasmid DNA that was genetically engineered to encode and express an anti-*P. falciparum* haptenic sequence as part of the HBcAg protein chain (discussed hereinafter), polysaccharide, and conjugate" vaccines that use specific pieces of the germ such as its protein, sugar, or capsid as the immunogen, and are illustrated by vaccines that are used to protect against Hib (*Haemophilus influenzae* type b) disease, hepatitis B, human papillomavirus (HPV), whooping cough, pneumococcal disease, meningococcal disease, and shingles.

The fifth type are the "toxoid" vaccines that create immunity to the parts of the germ that cause a disease instead of the germ itself. One illustrative toxoid vaccine protects against diphtheria, and another protects against tetanus.

The sixth type are "viral vector" vaccines of which only one is understood to be currently approved for emergency use in the U.S. That vaccine is the recombinant, replication-incompetent adenovirus type 26 expressing the SARS-CoV-2 spike protein vaccine developed by Janssen Pharmaceutical Companies Inc. of Johnson & Johnson.

The adjuvant CpG 1018 that is present in the Heplisav-B® anti-hepatitis B vaccine is said in the manufacturer's literature [*A UNIQUE APPROACH THAT HELPS CLOSE THE CLINICAL GAP IN PROTECTION*, 2021 Dynavax Technologies Corporation], "is taken up by the TLR9-expressing antigen-presenting cell to trigger a cascade of robust immunostimulatory responses. This may induce a highly specific, helper T-cell response to generate memory T and B cells."

It is important to note that the TLR9 immune response signalling cascade includes production of a Type I IFN response and the production of pro-inflammatory cytokines.

[Kawi et al., *Cell Death Differ* 13:816-825 (2006).] Those pro-inflammatory cytokines include IL-12, IL-6, IL-8 and TNFα [O'Neill et al., *Pharmacol Rev* 61:177-197 (2009)], and those pro-inflammatory cytokines have been associated with cytokine storms in different diseases. See, Yiu et al., *PLosONE* 7(10):e45027; Rowaiye et al., *J Inflamm Res* 14:1487-1510 (2021); Tisoncik et al., *Microbiol Mol Biol Rev* 76(1):12-32 (2012); and Diorio et al., *J Clin Invest* 130(11):5967-5975 (2020).

A cytokine storm syndrome (CSS), sometimes also referred to as cytokine release syndrome (CRS), refers to an umbrella of clinical states in which hyperinflammation and multi-organ disease arise from excessive cytokine release due to uncontrolled immune activation, and includes infectious, rheumatic, oncological, and immunotherapeutic aetiologies responsible for mortality in children and adults all over the world. Thus, the released cytokines induce white blood cells to continually activate more white blood cells to release more cytokines in a positive feedback loop [Lee et al., *Blood* 124(2):188-195 (July 2014)].

Severely ill COVID-19 patients can undergo a hyperinflammatory syndrome such as a cytokine storm and develop secondary hemophagocytic lymphohistiocytosis (sHLH), which causes acute respiratory distress syndrome (ARDS). ARDS causes about 50% mortality in these patients. Cytokine storms are seen in sepsis, non-infectious systemic inflammatory response syndrome (SIRS), macrophage activation syndrome (MAS), and secondary hemophagocytic lymphohistiocytosis. As such, cytokine storms are to be avoided.

Another contemplated embodiment is a vessel or a container such as a vial or bottle holding a concentrated pre-vaccine composition that contains an immunogen and the HX compound discussed above. The amounts of the two components are predetermined to provide a vaccine-effective amount and an adjuvant-effective amount of the immunogen and HX compound, respectively, to provide a mammalian HX compound-adjuvanted vaccine on dissolution or dispersion in a predetermined amount of a pharmaceutically acceptable diluent when the vaccine is prepared.

In this embodiment, the components of the mammalian HX compound-adjuvanted vaccine are typically in dry, powdered form as can be obtained by freeze-drying (lyophilization) an aqueous solution or dispersion of some or all of the components. Thus, for example where an aqueous composition is to be used for the formulated the vaccine, as that for protection against hepatitis B virus where the immunogen is HBsAg, the proteinaceous immunogen can be obtained from the growth medium and lysate of the recombinantly-transformed *Saccharomyces cerevisiae* used to produce the immunogen, followed by immunogen purification and lyophilization of an HBsAg-containing aqueous composition. One or more water-soluble buffering materials, desired osmolarity-providing materials, HX compound adjuvant compound such as disodium rose bengal, and additional reagents can be admixed in powdered form with the immunogen to provide a pre-vaccine that can be packaged, ready for addition of water for injection and agitation to dissolve or disperse the ingredients to prepare the mammalian HX compound-adjuvanted vaccine.

A further embodiment of the invention is an improved mammalian HX compound-adjuvanted vaccine composition that contains a vaccine-effective amount of a predetermined immunogen dissolved or dispersed in a pharmaceutically acceptable diluent in which the improvement comprises an adjuvant-effective amount of a halogenated xanthene compound as discussed before and hereinbelow that is also dissolved or dispersed with the immunogen in that pharmaceutically acceptable diluent. Vaccine excipients as have been discussed above and are further discussed below can also be present in a contemplated improved mammalian HX compound-adjuvanted vaccine composition.

Another aspect contemplates a method of inducing a Type I interferon response in a mammalian subject, preferably a human, in recognized need of treatment such as one that presents with a microbial infection that comprises administering an amount of a halogenated xanthene, a pharmaceutically acceptable salt, amide, ester, or aromatic derivative discussed above, effective to induce that Type I interferon response. The preferred halogenated xanthene is rose bengal disodium. When a $C_1$-$C_4$ alkyl ester halogenated xanthene is used, it is preferably a $C_2$ (ethyl) ester. When an aromatic derivative is used, it is preferably a benzyl, phenyl or a 2-, 3-, or 4-pyridyl (pyridyl) ester or amide, although other aromatic derivatives are also contemplated as is discussed hereinafter.

A further aspect contemplates a mammalian subject HX compound-adjuvanted vaccine for treating a solid cancerous tumor. This method utilizes a composition from a treated subject as described in U.S. Pat. No. 10,130,658 as the immunogen and thereby creates what can be referred to as an anti-self tumor vaccine.

Here, the immunogen is an enriched tumor-specific immune anti-cancer agent preparation that contains a tumor-specific immune anti-cancer agent composition. The components of that composition are induced by one or more intralesional (IL) administrations of a tumor-ablating amount of a halogenated xanthene compound, or a pharmaceutically acceptable salt thereof, into one or more solid cancerous tumors of a host mammal to contact the cancerous tissue, ablate the cancerous tumor and form tumor-ablated cell debris antigenic protein, and which components are collected from the host mammal about 1 to about 365 days after the one or more IL administrations.

Relative to amounts prior to IL administration, the composition contains immune cells that are peripheral blood mononuclear (PBM) cells and a statistically significantly enhanced concentration of halogenated xanthene-induced immune anti-cancer components that are one or both of a) a lymph-soluble cytokine selected from the group consisting of IL-2, TNF-α, LT, GM-CSF, IFN-γ, and HMGB1, b) immune cells that are peripheral blood mononuclear (PBM) cells and c) antibodies that bind to an antigen displayed on a whole tumor cell or to halogenated xanthene tumor-ablated cell debris antigenic protein. The immune cells that are peripheral blood mononuclear (PBM) cells have been cultured and preferentially expanded in vitro to form the enriched tumor-specific immune anti-cancer agent composition. The contemplated HX adjuvant, its amount, and the remainder of the contemplated vaccine components are as descried elsewhere herein.

Halogenated Xanthene (HX) Compounds

Our previous studies have identified halogenated xanthene (HX) compounds and particularly rose bengal [4,5,6,7-tetrachloro-2',4',5',7'-tetraiodofluorescein] (RB) as novel therapeutic agents with potent activity following intra-tumoral injection or topical application. Rose bengal is the prototypical member of the HX compound class of molecule described by Singer et al. in U.S. Pat. Nos. 8,530,675, 9,273,022, and 9,422,260.

These molecules have several medical uses, including as injectable oncology drugs as described by Eagle et al. in U.S. Pat. Nos. 9,107,887, 9,808,524, and 9,839,688 and as topical dermatology drugs as described by Dees et al. in U.S.

Pat. No. 8,974,363. Although RB has shown promise as an immuno-activating therapy for cancer [Liu et al., Oncotarget 7:37893 (2015)] and as an immuno-modulating therapy for inflammatory dermatoses [Krueger et al., *Psoriasis from Gene to Clinic* 2018], these molecules have not had a proposed role in direct activation of innate immunity.

Using equilibrium dialysis, more than 99.8% of RB is bound in serum from rats lacking serum albumin, indicating that several proteins are involved. In normal rats, 75-80% of the RB was recovered from the albumin fraction and the remaining 20-25% in other protein fractions [Tsao et al., *Drug Metab Dispos*, 16(3):482-489 (1988); and Meurman, *Acta medica Scan, Supp* 167, Chapters I, III, V, VII, X and XII (1960)]. We have confirmed that RB exhibits a high degree of plasma protein binding in rat plasma using the ultracentrifugation method, with 99.0% plasma protein binding observed at 1 μM and 99.2% at 10 μM; and that this affinity is higher in human plasma, with 99.8% to 99.9% plasma protein binding observed at 1 μM to 10 μM, respectively.

This affinity for biomolecules, in particular glycoproteins, appears to be the result of the unique physico-chemical properties of the HX compounds, which are amphipathic. For example, RB has a solubility of at least 10% (100 mg/mL) in water, 3% (30 mg/mL) in ethanol and 6% (60 mg/mL) in 2-methoxyethanol [Floyd J. Green, *Sigma-Aldrich Handbook of Stains, Dyes and Indicators*, Aldrich Chemical Company, Inc., Milwaukee, WI, pages 637-638 (1990)].

When administered via intravenous methods (IV) to humans, the HX compounds are excreted via the bile without metabolism with a circulatory half-life of approximately 30 minutes; this led to historic use as an IV diagnostic of hepatic function. Starting with initial clinical demonstration by Delprat et al., *Arch Intern Med* 34:533-541 (1924), intravenous RB became routinely used as a diagnostic for hepatic impairment based on differential excretion. Introduction of $^{131}$I radiolabeled RB in the 1950s expanded use as an imaging agent [Taplin et al., *J Lab Clin Med* 45(5): 665-678 (1955)] that allowed direct imaging of the liver via gamma ray detection.

In clinical use, radio-iodinated RB was often diluted with non-radiolabeled RB. The approved indication in the U.S. was for use as a diagnostic aid in determining liver dysfunction and for liver imaging at doses of up to 25 μCi of $^{131}$I RB (approximately 12 mg of RB) together with a blocking dose of non-radiolabeled RB (100 mg given 10 minutes prior to radiolabeled product dosing) to retard the excretion rate of the radiolabeled product to permit more time for liver scanning. We have repeated this procedure with non-radiolabeled RB to confirm the safety and pharmacokinetic properties of systemically administered RB using modern clinical tools and standards.

Yoshimoto et al., *J Food Hyg Soc Japan*, 25(4):352-355 (1984) reported studies of the effects of rose bengal orally administered to young male Wistar rats at 300 mg/kg/day dissolved in distilled water. Those workers reported no influence on growth rate, but RB caused a significant decrease in relative liver weight. No effect on $H^3$-UTP incorporation into RNA or RNA content in liver nuclei was noted. Similar concentrations of Ponceau 3R or Amaranth were reported to stimulate RNA synthesis in vivo.

The similarly useful halogenated xanthene compounds listed below and their pharmaceutically acceptable salts can have molecular weights that differ from each other by about a factor of three (See, Table 3, U.S. Pat. No. 7,390,688 at columns 15-16). It is preferred that an exact amount of a specific HX compound to be used is calculated based on molecular weights for each such compound or that of RB.

A contemplated HX compound includes rose bengal (4,5,6,7-tetrachloro-2',4',5',7'-tetraiodofluorescein; RB) that is particularly preferred, erythrosin B, phloxine B, 4,5,6,7-tetrabromo-2',4',5',7'-tetra-iodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein.

The reader is directed to Berge, *J. Pharm. Sci.* 1977 68(1):1-19 for lists of commonly used pharmaceutically acceptable acids and bases that form pharmaceutically acceptable salts with pharmaceutical compounds, such as the above halogenated xanthenes. Illustrative cations include alkali metals such as sodium, potassium, as well as ammonium and alkaline earth salts such as magnesium and calcium. The disodium salt of rose bengal is particularly preferred.

A $C_1$-$C_4$ alkyl ester of one of the above halogenated xanthene compounds can also be used, with the $C_2$; i.e., ethyl ester, being preferred. Thus, in vitro studies using each of RB, ethyl-Red 3 (erythrosine ethyl ester; 2',4',5',7'-tetraiodofluorescein ethyl ester), 4,5,6,7-tetrabromo-2',4',5',7'-tetraiodofluorescein and ethyl-Phloxine B (4,5,6,7-tetrachloro-2',4',5',7'-tetrabromofluorescein ethyl ester) exhibited similar anti-tumor activities against CCL-142 renal adenocarcinoma. When an aromatic ester is used, it is preferably a benzyl or phenyl ester.

The carboxyl group of an HX compound can also be used to form an amide group. The amide nitrogen atom can be unsubstituted [—C(O)—NH$_2$], monosubstituted with a $C_1$-$C_4$ alkyl group [—C(O)—NHR$^1$, where R$^1$ is $C_1$-$C_4$ alkyl], or be disubstituted with two independently selected $C_1$-$C_4$ alkyl groups, [—C(O)—NR$^1$R$^2$, where R$^1$ and R$^2$ are each independently the same or different $C_1$-$C_4$ alkyl groups]. Alternatively, the R$^1$ and R$^2$ groups together with the amido nitrogen atom form a 5- or 6-membered ring.

Additionally, the HX compound carboxyl group can form an aromatic derivative that is an ester or monosubstituted amide. The aromatic ring of such a derivative is a single 5- or 6-membered aromatic ring, or a 5,6- or 6,6-fused aromatic ring system that contains 0, 1 or 2 hetero ring atoms that are independently nitrogen, oxygen, or sulfur.

An aromatic derivative whose aromatic ring portion is phenyl, benzyl or 2-, 3-, or 4-pyridyl (pyridyl) is presently preferred. However, other aromatic single and fused ring-containing esters and amides are contemplated. Illustrative examples of such aromatic ester and amide derivative groups are shown and named below, wherein Z is O or NH, line-Z indicates the ring-oxygen or ring-nitrogen can be from any available carbon of the ring, and Z-line crossed by a wavy line indicates that the depicted alkoxy or amino group is a portion of another molecule, the esterified or amidified HX molecule.

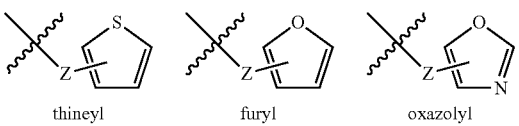

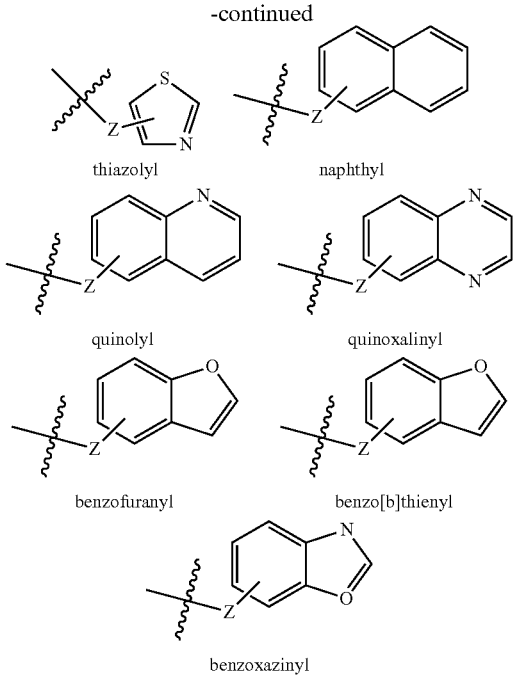

thiazolyl naphthyl quinolyl quinoxalinyl benzofuranyl benzo[b]thienyl benzoxazinyl An aliphatic or aromatic derivative of one of the above HX compounds can also be used, such as 2,3,4,5-tetrachloro-6-(6-hydroxy-2,4,5-triiodo-7-isopropyl-3-oxo-3H-xanthen-9-yl) benzoic acid disodium [4,5,6,7-tetrachloro-2',4',5'-triiodo-7'-isoproplyfluorescein], represented by Figure is in Singer et al. U.S. Pat. No. 8,530,675, and similar aliphatic or aromatic derivatives formed via attachment of one or more aliphatic or aromatic moieties at one or more of positions 2, 3, 4, 5, 2', 4', 5', or 7'.

A preferred form of RB is rose bengal disodium that has the structural formula below:

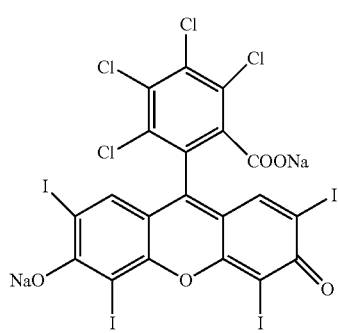

Further details of the medicinal use a pharmaceutical composition containing an above-noted HX compounds are described in U.S. Pat. Nos. 5,998,597, 6,331,286, 6,493,570, 7,390,688, 7,648,695, 8,974,363, 9,107,887, 9,808,524, 9,839,688, 10,130,658 and 10,471,144, whose disclosures are incorporated by reference herein in their entireties.

A contemplated HX, its pharmaceutically acceptable salt or ester or amide as discussed above, is typically used dissolved or dispersed in an adjuvant amount in an aqueous mammalian HX compound-adjuvanted vaccine composition. An adjuvant amount of an HX molecule, salt, ester or amide (compound), as previously discussed, is that amount that induces a Type I IFN immune reaction. Such an amount is also an amount of HX compound that is less than a cytotoxic amount, and preferably less than about 75% of a cytotoxic amount.

A cytotoxic amount is the $IC_{50}$ value amount for an oncology indication (e.g., neuroblastoma, leukemia, melanoma or other tumor), whereas for infectious disease, the cytotoxic amount is the $IC_{50}$ for normal tissue (e.g., cultured fibroblasts, kidney cells, and the like). The data shown in Tables 1 and 2 of U.S. Pat. No. 11,058,664 illustrate that the $IC_{50}$ value for use of RB against thirteen pediatric solid tumor cell lines in vitro is about 50 to about 100 μM, with a median of about 70 μM, for exposures at 96 hours post treatment. Similar treatments of normal fibroblast cell lines and a primary bone marrow sample provided $IC_{50}$ values of about 73-143 μM, with a mean of 104 μM. Similar data are reported by one of the inventors and his research group for eleven pediatric leukemia cell lines with a mean $IC_{50}$ value of 93 μM and a mean $IC_{50}$ value of 122 μM for three primary leukemia samples [Swift et al., *Blood* 132 (Supplement 1):5207 (2018)].

Given that the molecular weight of RB disodium is 1,018 g/mole, the above cytotoxic $IC_{50}$ values calculates to about 50 to about 100 mg of RB/liter. Those values translate to approximately $10^{-4}$ to about $10^{-5}$ molar based on the $IC_{50}$ values. Thus, a typical adjuvant-effective amount of a HX compound in a mammalian HX compound-adjuvanted vaccine composition based on RB as the HX compound is about 35 to about 75 mg/liter or about $7.5 \times 10^{-5}$ to about $7.5 \times 10^{-6}$ molar.

The short human circulatory half-life of the HX compounds (about 30 minutes) facilitates effective application of these molecules for acute STING activation, maximizing innate immune signaling potential, while avoiding chronic activation that could lead to counterproductive inflammatory response, possible autoimmune disease or promotion of tumorigenesis. As is seen from the in vitro results shown in FIGS. 1C-1R, the effects of RB on enhancing the cytokine production occurred within 48 hours in each of the sixteen cytokines.

The Immunogen

A contemplated vaccine contains an immunogen that can be a killed or incapacitated infectious agent such as a virus, bacterium, fungus, or single-celled parasite. The immunogen can also be one or more proteins or peptidyl protein portion(s) present in the infectious agent from which protection is sought. The immunogen can further be a saccharide-containing portion of the infectious agent. These other than whole infectious agent immunogens can be obtained from the infectious agent itself, made via synthetic chemistry or by recombinant techniques as noted earlier in the discussion of the vaccine types.

The immunogen is present in the vaccine in a vaccine-effective amount. That amount can be the amount of the immunogen present in a governmentally approved vaccine. For a not yet approved vaccine, that amount is the amount needed in the absence of the HX compound adjuvant to induce a desired immune response in the subject mammal to which the vaccine is administered. Thus, protective antibodies and/or T cells are formed resulting from administration of a vaccine containing a vaccine-effective amount of the immunogen.

Illustrative viral infectious agents (pathogens) from which protection is sought include influenza, hepatitis viruses A, B, C, and D, herpes viruses such as Varicella zoster (chickenpox), Herpes simplex 1 and 2 (HSV1 and HSV2), human papilloma virus (HPV), and the like. Illustrative bacterial pathogens include *E. coli*, *E. faecalis*, *S. aureus*, and the like.

An illustrative unicellular parasite is the malaria sporozoite of *P. falciparum, P. vivax, P. bergeii* or *P. yoelli*. Illustrative fungal infective agents include *Candida albicans, Candida glabrata, Candida parapsilosis, Candida tropicalis*, and *Candida krusei*.

Illustrative proteinaceous immunogens and disease-related marker molecule peptides are disclosed in WO 2020028532 with citations to their published sources.

U.S. Pat. No. 6,942,866 includes the following peptidyl epitopes:

Malarial B Cell Epitopes
 *P. falciparum*
 *P. vivax*
 *P. bergeii*
 *P. yoelli*
Malarial Universal T Cell Epitope
 *P. falciparum*
 *P. vivax*
 *P. yoelli*

U.S. Pat. No. 8,017,127 includes the following peptidyl epitopes:

Influenza A M2 Protein B Cell Epitopes

As is noted in U.S. Pat. No. 8,017,127, the M2 protein is expressed in cells infected by the influenza A strains. The N-terminal residues 1-24 of the M2 protein extends through the infected cell's membrane. That extracellular portion of the protein is referred to as M2e. Consequently, use of the influenza A extracellular M2e portion of that protein as part of the immunogen could provide protection from all of the influenza strains. Thus, the yearly changes in influenza vaccine selection can be avoided.

U.S. Pat. No. 4,599,231 includes the following peptidyl epitopes:

Hepatitis B Virus Surface Antigen

The hepatitis B virus surface antigen (HBsAg) provides both B cell and T cell polypeptide epitopes. A number of each epitope type as disclosed in U.S. Pat. No. 4,599,231 are set out below in the table along with their peptide denominations, and parenthesized sequence position from the N-terminus, as recited in that patent based on DNA from an ayw donor (P49) and an adw donor (P72 and P73).

B Cell Epitope

U.S. Pat. No. 5,180,806 includes the following peptidyl epitopes:

Human Papilloma Virus (HPV) Marker Peptides

Papillomaviruses induce benign, dysplastic and malignant hyperproliferations of skin or mucosal epithelium. More than 50 types (strains) of human papillomavirus (HPV) have been identified. In humans, different papillomavirus types are known to cause distinct diseases. For example, HPV types 1 and 2 cause common warts, and types 6 and 11 cause condylomas and genital flat warts. In contrast, HPV types 16, 18 and 33 are carried in most cervical cancers and do not cause the usual condyloma, but rather persist diffusely in the cervical endothelium exhibiting only minimal pathologic changes. It is thought that the HPV types associated with cervical cancer are maintained in a latent state in cervical endothelium tissues for years after initial infection and then progress in some cases to cause cervical cancer.

U.S. Pat. No. 5,180,806 discloses several peptide sequences that induce the production of antibodies when linked to a carrier. Illustrative peptide markers of type 16-related HPV sequences disclosed in U.S. Pat. No. 5,180,806. That patent also discloses peptide sequences from type 18 and type 33, as well as sequences encoded by the E2 ORF of HPV types 6, 11, 18 and 33.

The above peptidyl epitopes are typically not effective by themselves to induce an immune response and are referred to in the art as haptens. Rather, they must be linked to a carrier molecule, usually a protein, that is itself immunogenic, although not necessarily against the infectious agent from which protection is sought. Illustrative examples of such carrier molecules are keyhole limpet hemocyanin (KLH) and the hepatitis B core protein/particle (HBcAg).

U.S. Pat. No. 6,231,846 to Birkett teaches the use of HBcAg that has been modified with an added amine-containing amino acid residue such as lysine to which a peptidyl hapten can be bonded to produce a construct that is itself immunogenic against the desired infectious agent. The hepatitis B core protein self-assembles to a generally spherical particle that includes about 180 individual, identical proteins. That patent also lists about 70 peptidyl haptens for several infectious agents. Also listed are several carbohydrate haptens along with literature or patent references as to the efficacy of each against its target infectious agent.

U.S. Pat. No. 4,544,500 to Bittle et al. teaches the use of KLH as a carrier for a peptidyl hapten corresponding to a portion of the foot-and-mouth disease virus (FMDV) $VP_1$ protein, particularly at positions 141-160 from the amino-terminus. KLH was also the carrier for peptide haptens having a sequence of a portion of the hemagglutinin protein of an influenza virus A (H3N2) described in U.S. Pat. No. 4,625,015 to Green et al.

U.S. Pat. No. 6,942,866 to Birkett teaches an anti-*Plasmodium falciparum* immunogen that was expressed in *E. coli* as modified HBcAg particles. The transformed *E. coli* contained a plasmid DNA that was genetically engineered to encode and express an anti-*P. falciparum* haptenic sequence as part of the HBcAg protein chain so that each expressed HBcAg protein contained the haptenic sequence.

Vaccine Composition

A contemplated mammalian HX compound-adjuvanted vaccine composition can and usually does contain the immunogen and the HX compound adjuvant, and also one or more excipients, as noted previously. Because such a composition is typically intended for parenteral administration as by an IV method, such a composition should also contain an electrolyte, and preferably have approximately physiological osmolality and pH value.

A preferred concentration of singly charged electrolyte ions in a pharmaceutically acceptable aqueous medium is about 0.5 to about 1.5% (w/v), more preferably at about 0.8 to about 1.2% (w/v), and most preferably at a concentration of about 0.9% (w/v). The about 0.9% (w/v) concentration is particularly preferred because it corresponds to an approximately isotonic aqueous solution. In a further preferred embodiment, the electrolyte in a contemplated pharmaceutical composition is sodium chloride.

Electrolytes at such levels increase the osmolality of a pharmaceutically acceptable aqueous medium. Thus, as an alternative to specifying a range of electrolyte concentrations, osmolality can be used to characterize, in part, the electrolyte level of the composition.

Tonicity agents (or tonicity-adjusting agents) such as sugars like mannitol and dextrose, $C_3$-$C_6$ polyhydroxy compounds such as propylene glycol, glycerol and sorbitol, isotonic salts such as sodium or potassium chloride, and/or buffering agents such as phosphate salts, citric acid, malic acid, acetic acid and other food acids and their salts can be used.

It is preferred that the osmolality of a composition be greater than about 100 mOsm/kg, more preferably that the osmolality of the composition be greater than about 250 mOsm/kg, and most preferably that it be about 300 to about 500 mOsm/kg.

It is preferred that the pH value of a pharmaceutically acceptable aqueous medium be about 4 to about 9, to yield maximum solubility of the HX compound in an aqueous vehicle and assure compatibility with biological tissue. A particularly preferred pH value is about 5 to about 8, and more preferably between about 6 to about 7.5. Most preferably, the pH value of a vaccine composition is 7.35 to 7.45, or more easily, 7.4, the pH value of blood plasma [P. Karlson, Introduction to Modern Biochemistry, Academic Press, Inc., New York, NY, page 366 (1963)]. At these pH values, that those compounds containing a free carboxyl group (neither esterified nor amidified) typically remain in dibasic form, rather than the water-insoluble lactone that forms at low pH values.

The pH value of a pharmaceutically acceptable aqueous medium can be regulated or adjusted by any suitable means known to those of skill in the art. The composition can be buffered or the pH value adjusted by addition of acid or base or the like. As the halogenated xanthenes, or physiologically acceptable salts thereof, are weak acids, depending upon halogenated xanthene concentration and/or electrolyte concentration, the pH value of the composition may not require the use of a buffer and/or pH modifying reagent. It is especially preferred, however, that the composition not contain any buffer (be free of buffer or buffer-free), permitting it to conform to the biological environment once administered.

One or more additional adjuvants can also be present as an additional excipient. Aluminum-containing compounds are the most commonly used vaccine adjuvants in the United States.

The ratio of immunogen (Im) weight to weight of aluminum (Al) ranges widely from about 0.3 to about 2.7 mg Im/Al. The weight ratios also differ from immunogen to immunogen as to whether aluminum oxyhydroxide or aluminum hydroxyphosphate or both are used [Clapp et al., *J Pharm Sci* 100(2):388-401 (2011)].

There are two aluminum-based adjuvants (ABAs) commonly used in vaccines. Alhydrogel® is a semicrystalline form of aluminum oxyhydroxide (AH) and AdjuPhos® is an amorphous salt of aluminum hydroxyphosphate (AP). A sulphate salt of the latter (AAHS) is also listed as being one component of an adjuvant system used in vaccinations against HPV. [Shardlow et al., *Allergy Asthma Clin Immunol* 14:80 (2018)].

Aluminum-adjuvanted vaccines have a long history of clinical successes and a commensurately long history of vaccine-related adverse events. As there is no requirement to demonstrate the safety of ABAs, one could quickly surmise that adverse events following vaccination are the direct or indirect effects of ABAs [Shardlow et al., *Allergy Asthma Clin Immunol* 14:80 (2018)].

A so-called "immune checkpoint inhibitor" or an "immune checkpoint-like inhibitor" can also be used as an adjuvant. An immune checkpoint inhibitor is a drug that binds to and blocks certain checkpoint proteins made by immune system cells such as T cells and also by some cancer cells. When not blocked, those proteins inhibit immune responses, helping keep immune responses in check, such as by keeping T cells from killing cancer cells. Blocking those immune checkpoint proteins releases the "brakes" on the immune system permitting T cells to become activated.

A useful immune checkpoint inhibitor is preferably a human or humanized monoclonal antibody or binding portion thereof (paratope) whose administration blocks the action of those certain proteins, thereby permitting the immune system to recognize the cancer cells as foreign and assist in eliminating those cancer cells from the body. Illustrative immune checkpoint inhibitors include the anti-CTLA-4 (cytotoxic T lymphocyte-associated antigen 4) monoclonal antibodies ipilimumab and tremelimumab that are designed to counter down-regulation of the immune system by blocking CTLA-4 activity and thus augment T-cell response against cancer. Similarly, monoclonal antibodies such as pidilizumab, nivolumab, lambrolizumab and pembrolizumab bind to PD-1 (programmed death 1) receptor to counter down-regulation of the immune system and augment T-cell responses to cancerous cells. Three antibodies that target the immune checkpoint protein ligand (PD-L1) for the PD-1 receptor (PD-L1) are atezolizumab, avelumab and durvalumab. Initial work with antibodies to the PD-1 receptor ligands, PD-L1 and PD-L2, such as BMS-936559 and MEDI4736 (durvalumab) to PD-L1, also indicate inhibition of down-regulation of the immune system and an augmented T-cell response against cancer.

Another group of antibodies with checkpoint inhibitor-like activity immunoreact with the cell surface receptor OX40 (CD134) to stimulate proliferation of memory and effector T-lymphocytes, and thereby stimulate a T-cell-mediated immune responses. Exemplary such humanized anti-OX40 monoclonal antibodies include those presently referred to in the literature as gsk3174998 (IgG1), pogalizumab (MOXR0916), MED10562 and the human anti-OX40 IgG2 antibody designated PF-04518600 (PF-8600).

A further group of antibodies with checkpoint inhibitor-like activity immunoreact with the T cell receptor with immunoglobulin and ITIM domains (TIGIT) is exclusively expressed on lymphocytes, including CD8+ T cells, memory and regulatory CD4+ T cells, follicular CD4+ T cells and NK cells [Ge et al., *Front. Immunol.* 12:699895 (July 2021)]. Illustrative anti-TIGIT monlclonal antibodies include those known in the literature as EOS-448 (GlaxoSmithKline), AGEN1777 (Bristol Myers Squibb), domvanalimab (AB154; Gilead Sciences) and tiragolumab (Roche). The anti-TIGIT antibodies have thus far been utilized mostly in cancer immunotherapy.

Intact monoclonal antibodies, as well their paratope-containing portions (binding site-containing portions) such as Fab, Fab', F(ab')$_2$ and Fv regions, as well as single-stranded peptide binding sequences can be useful as immune checkpoint protein inhibitors. Intact checkpoint inhibiting monoclonal antibodies have half-lives in a human body of about one to three weeks [e.g., Yervoy® (ipilimumab) terminal $t_{1/2}$=15.4 days; package insert 12/2013; Keytruda® (pembrolizumab) terminal $t_{1/2}$=23 days; package insert 03/2017], and single-stranded oligo or polypeptides tend to have shorter half-lives in vivo.

Results

Halogenated Xanthenes Activate STING

It has been found that rose bengal (RB) is a promoter of STING dimerization and a resulting Type I interferon response using a well-established acute monocytic leukemia (AML) cell line (THP-1) as a model to study STING activation in vitro. Cells were treated with RB and the endogenous induction of STING was evaluated by Western blot analysis using cyclic guanosine monophosphate-adenosine monophosphate (cGAMP) as a positive control.

These studies were carried out using RB at 100 μM, or about 0.01% RB. Cytokine assays were carried out prior to the addition of RB to the cell culture medium (0), and at 8, 24 and 48 hours thereafter.

Proteins that associate with STING in the presence of RB were purified by immunoprecipitation and analyzed by mass spectrometry (LC-MS/MS). The culture supernatants from RB-treated cells were probed for a panel of 42 immune cytokines using the Bio-Plex® multiplex bead-based assay system (Bio-Rad Laboratories, Inc.).

Figure 1B:
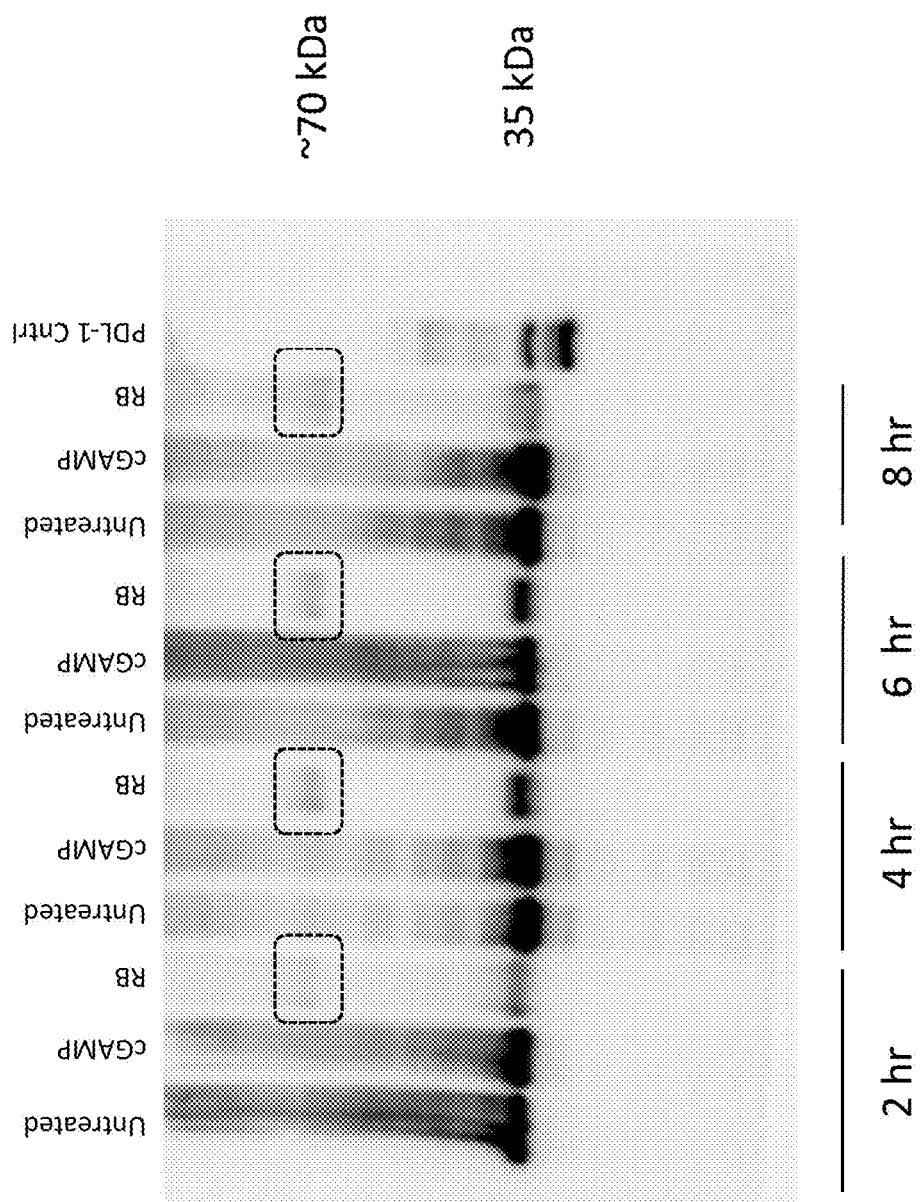
Figure 1D:
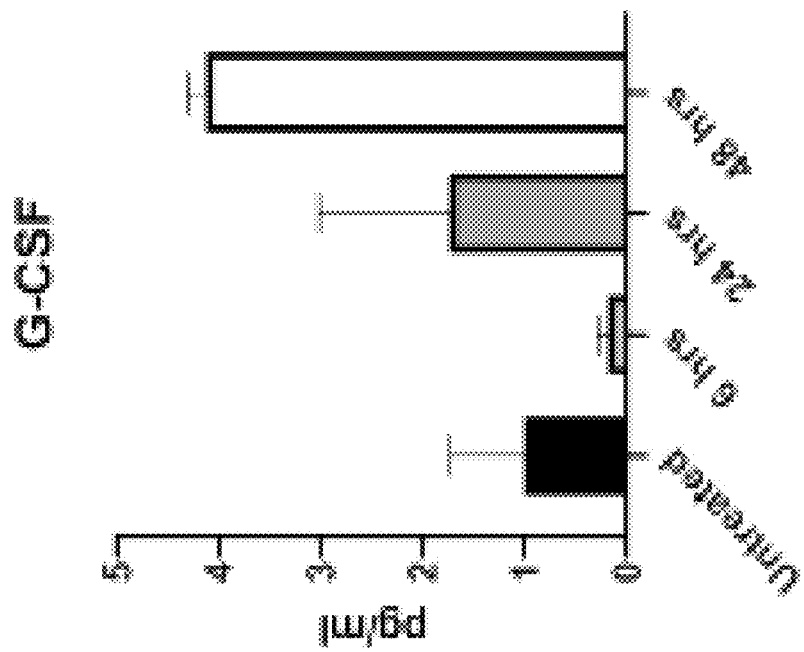
FIGS. 1C through 1R provide graphs of assayed amounts of the noted cytokines and chemokines from prior to RB contact with the THP-1 AML cells and at 6, 24, and 48 hours thereafter.

Exposure of THP-1 AML cells to RB led to the appearance of a new about 70-KD STING dimer band detected by specific antibodies FIGS. 1A and 1B (dashed boxes in the pictured gels). Compared to cGAMP controls, no induction of PDL-1 was noted. Mass spectrometric analysis of immuno-precipitates of STING in these cells showed the presence of heat shock proteins (HSPs) 60, 70 and 90 as well as polyadenylate binding protein 1 (PABP1) to the dimerized STING complex.

Figure 1C:
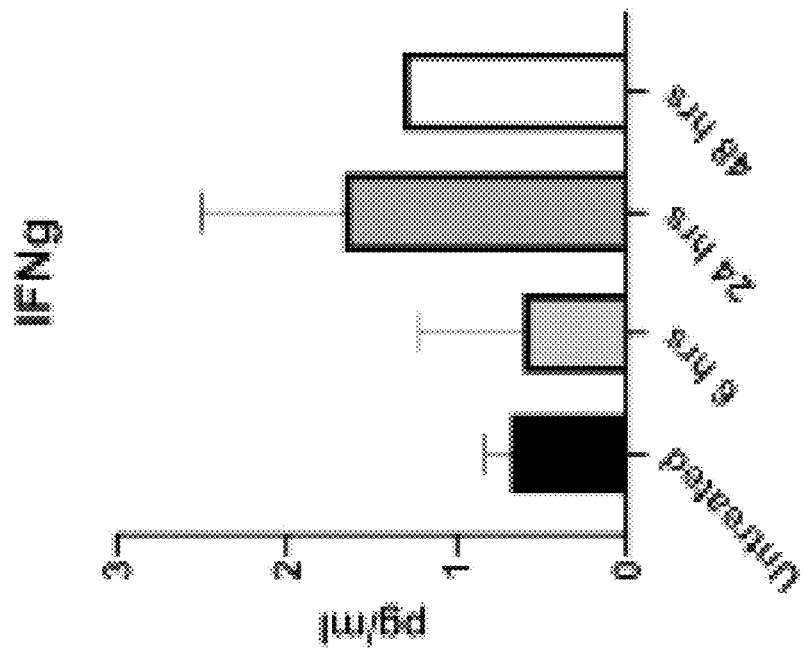
Figure 1F:
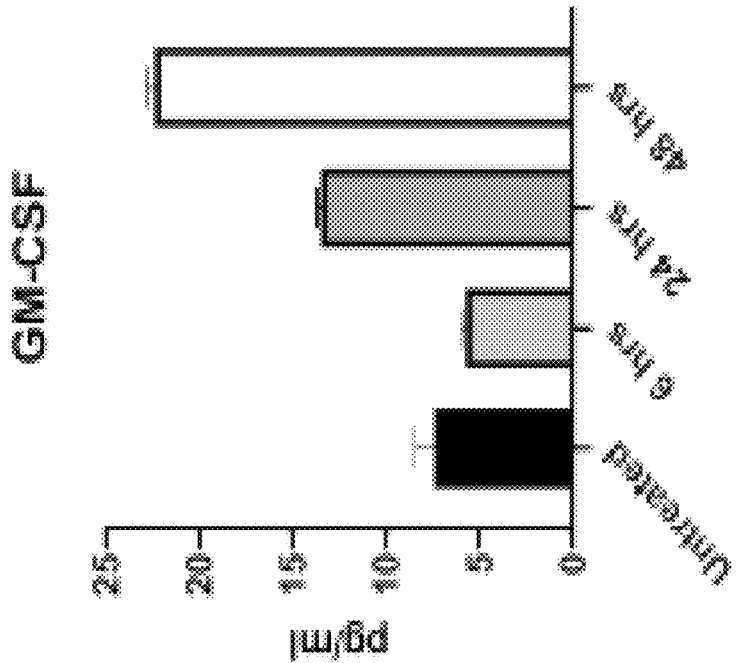
Figure 1E:
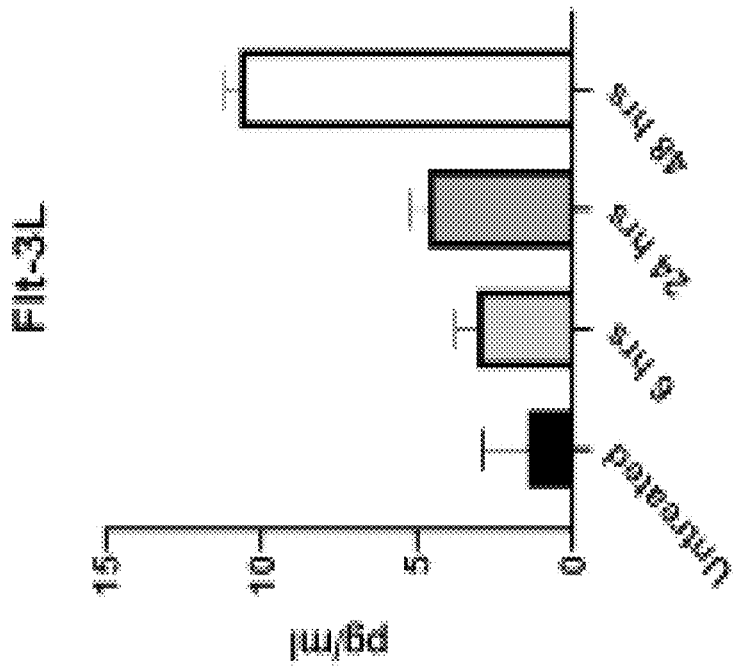
Figure 1H:
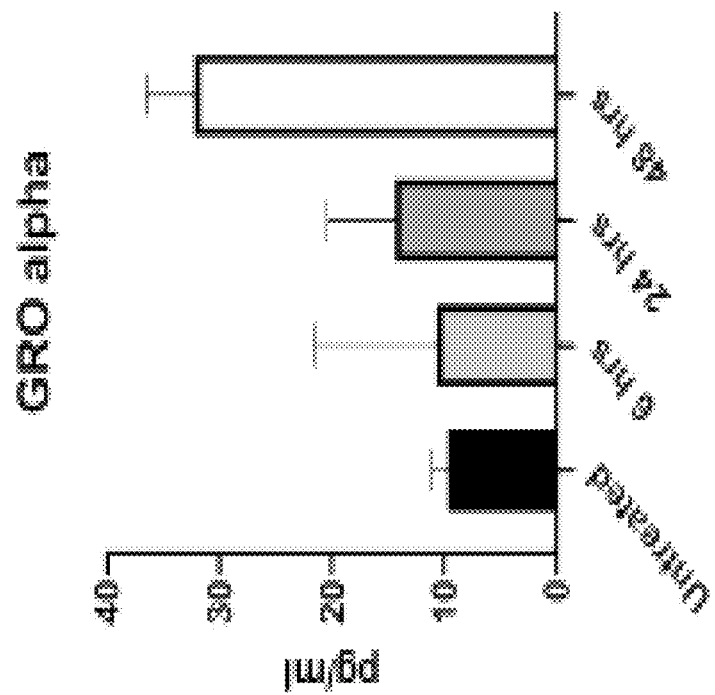
Figure 1G:
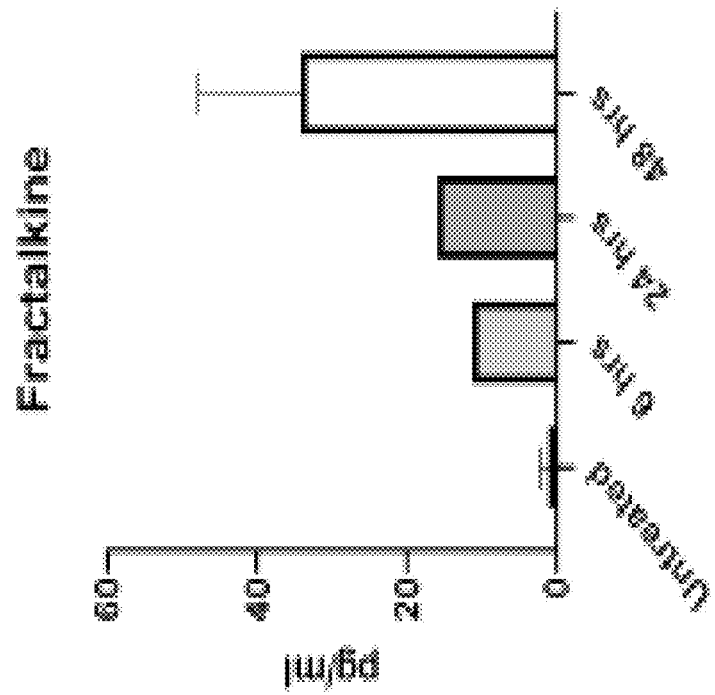
Figure 1L:
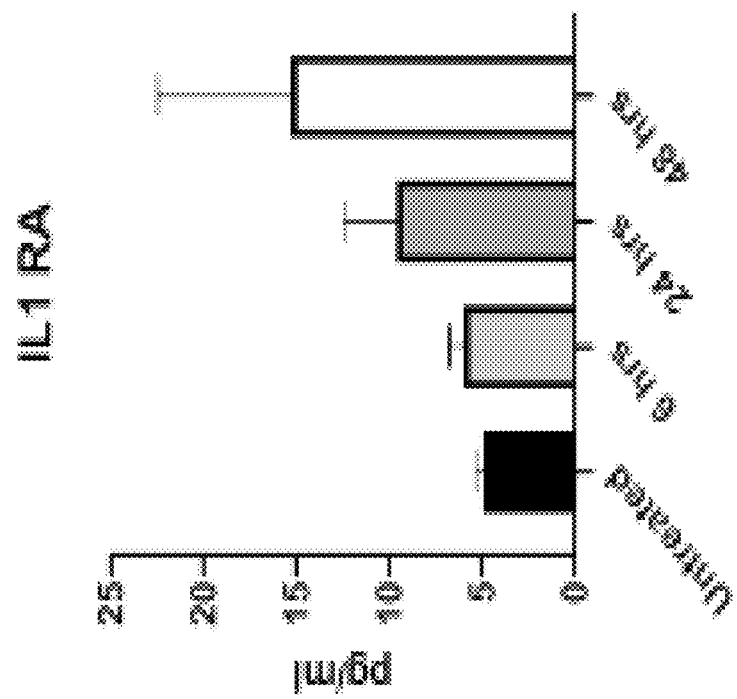
Figure 1K:
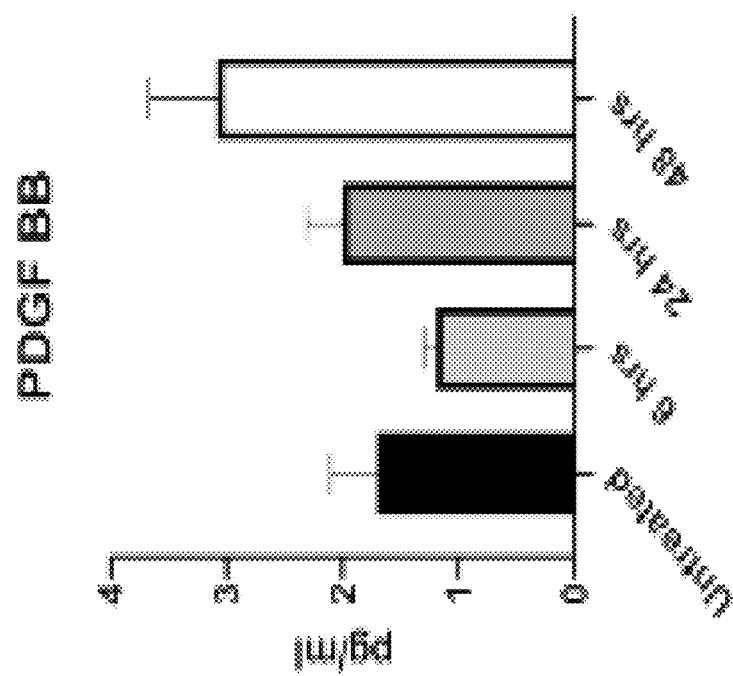
Figure 1N:
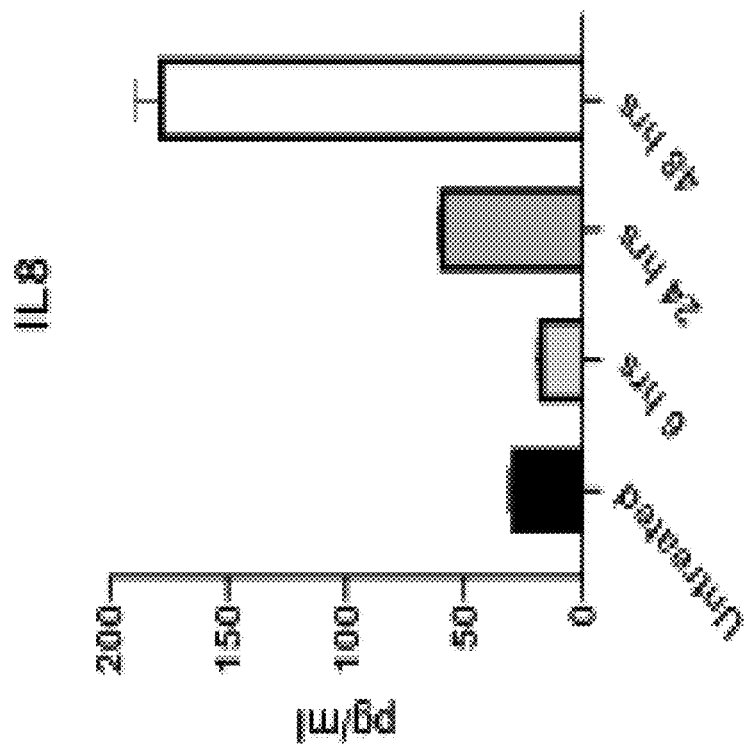
Figure 1M:
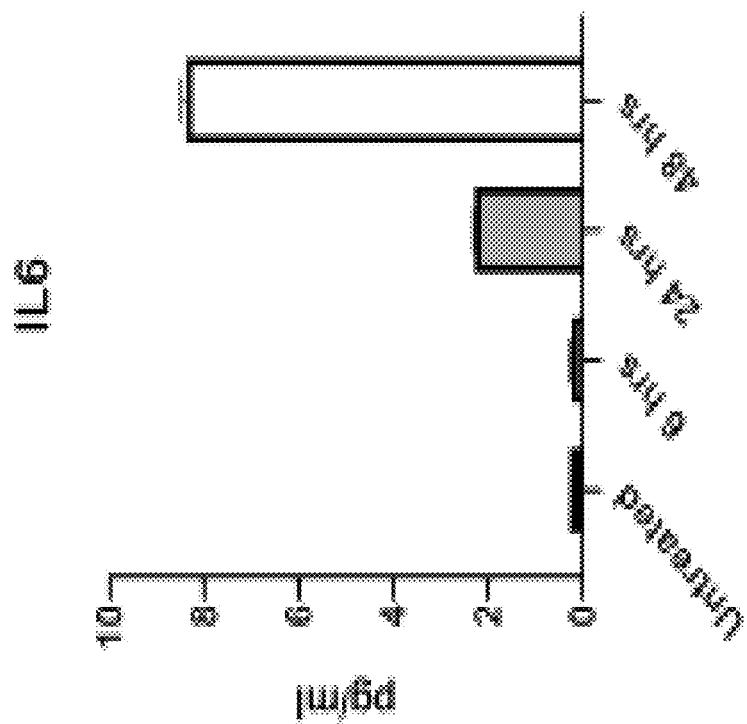
Figures 1O, 1P:
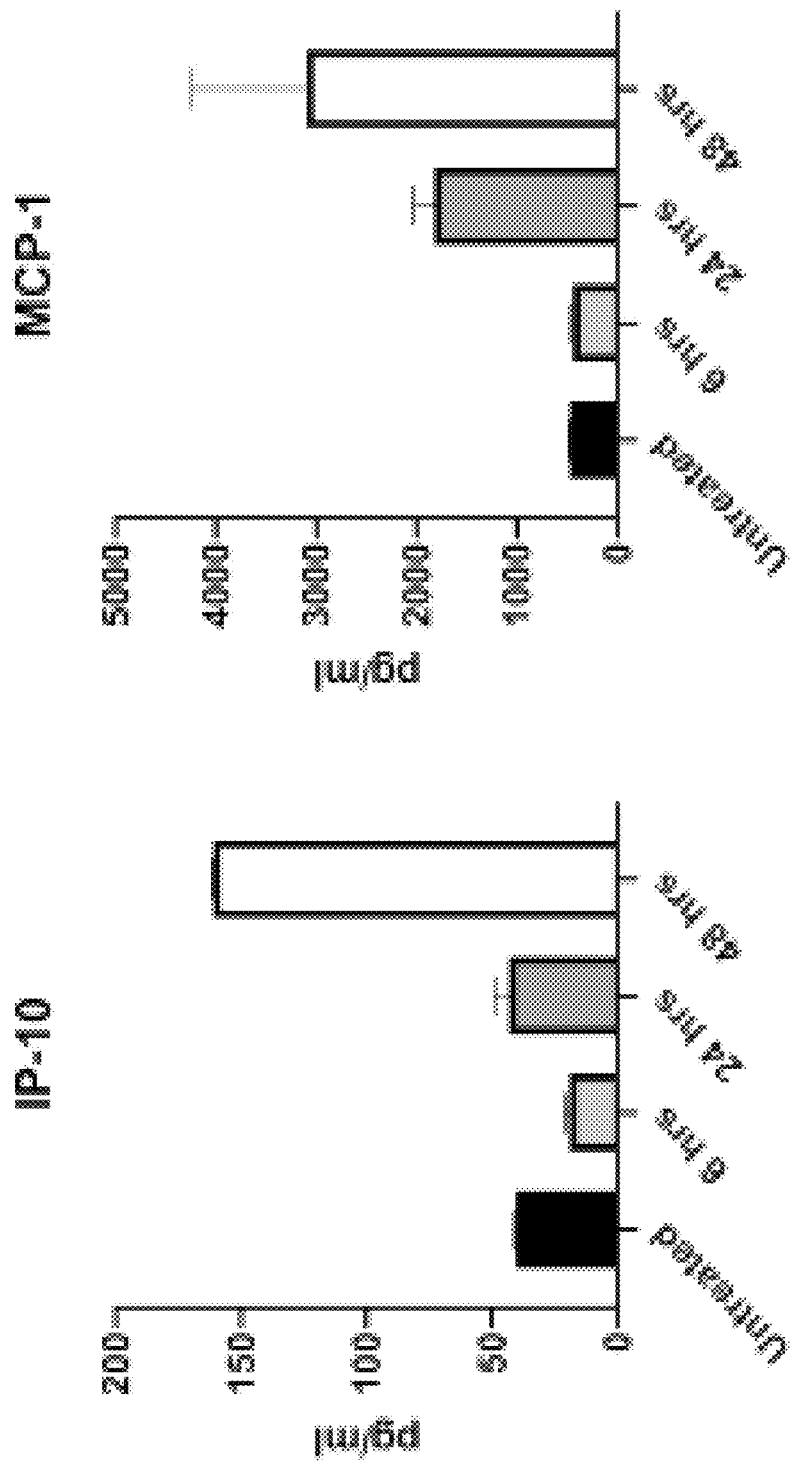
Figure 1Q:
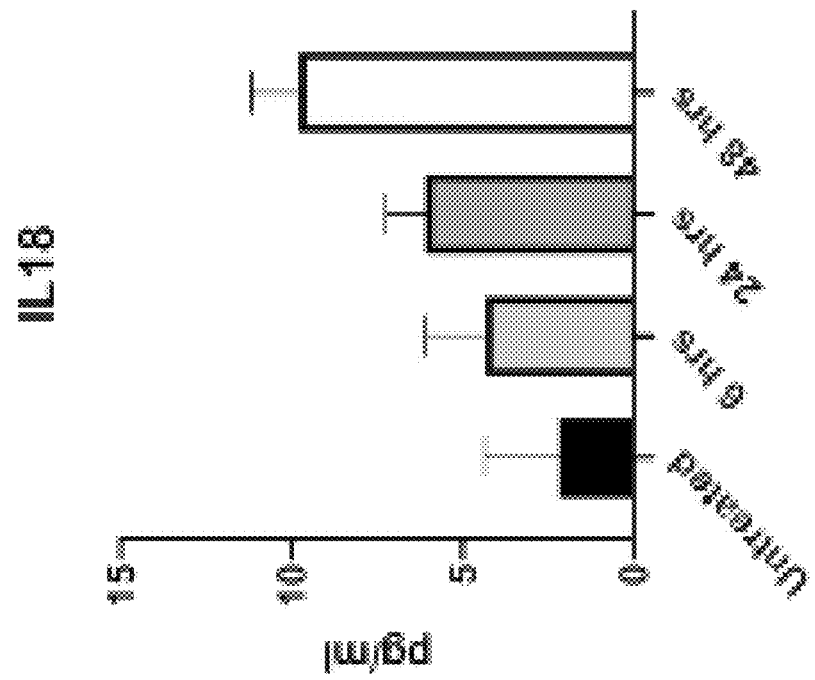
Figure 1R:
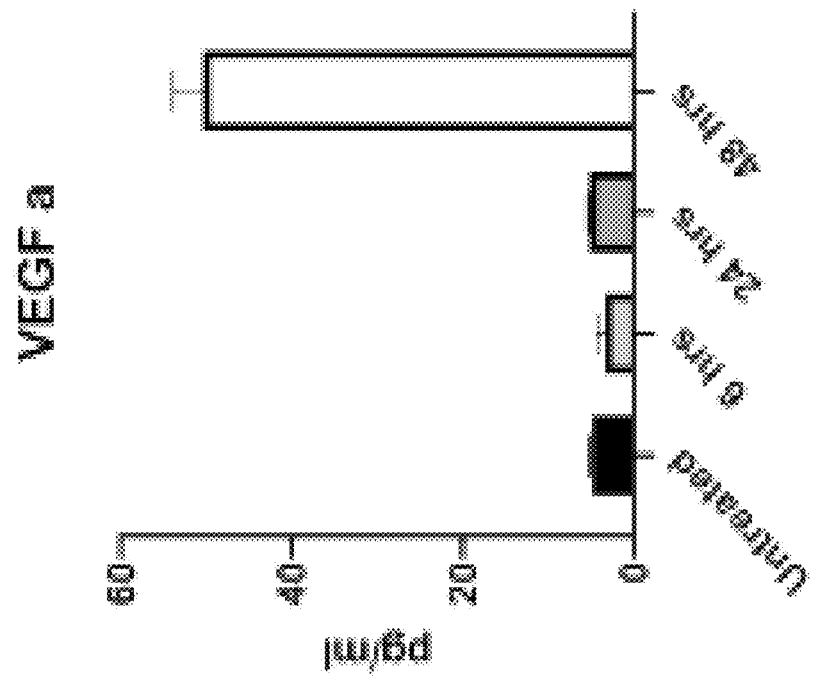

The chemokine assays showed specific upregulation of a distinct set of pro-inflammatory and cytotoxic T-cell recruitment cytokines (FIGS. 1C-1R). Thus, as shown, a peak in the induction of monocyte chemoattractant protein-3 (MCP-3) and IFN-gamma was seen at 24 hours (>2 fold) and an approximately 10-fold increase in each of IL-6, IL-8 and interferon-gamma-induced protein 10 (IP-10) was seen 24 hours following exposure to RB. A significant increase in MCP-1 levels were also noted.

These results demonstrate RB-induced STING dimerization and HSP association leading to an acute pro-inflammatory and immune response (i.e., within 24-48 hours). Additional in vitro studies confirmed that RB induces STING dimerization in solution (i.e., that the effect is not dependent on action within cancer cells).

The AML model and subsequent investigation illustrates that the HX compounds, such as for example RB, can induce acute STING dimerization. This has important implications in oncology where STING-mediated immune activation can play a pivotal role in innate and adaptive immune system responses in anti-tumor therapy, either as a single-agent immunotherapy such as with injectable oncology drugs as described by Dees et al., U.S. Pat. No. 7,648,695, or where such drugs are used in combination therapy with other drugs as described by Eagle et al., U.S. Pat. No. 9,107,887.

These results also indicate that HX compound-based induction of STING dimerization has important implications in virology where STING-mediated immune activation can play a pivotal role in innate and adaptive immune system response in anti-viral therapy, either as a single-agent anti-viral drug or in combination therapy with other anti-viral drugs. An adjuvant amount of an HX molecule or salt (compound), as previously discussed, is that amount that induces STING dimerization (i.e., a STING dimerization-inducing amount) and is further defined as an amount of HX compound that is less than a cytotoxic amount, and preferably less than about 75% of a cytotoxic amount. A cytotoxic amount is the $IC_{50}$ amount for an oncology indication (e.g., neuroblastoma, leukemia, melanoma, or other tumor), whereas for infectious disease, the cytotoxic amount is the $IC_{50}$ for normal tissue (e.g., cultured fibroblasts, kidney cells, and the like).

The short human circulatory half-life of the HX compounds (about 30 minutes) facilitates effective application of these molecules for acute STING activation, maximizing innate immune signaling potential while avoiding chronic activation that could lead to counterproductive inflammatory response, possible autoimmune disease or promotion of tumorigenesis. As is seen from the in vitro results shown in FIGS. 1C-1R, the effects of RB on enhancing the cytokine production occurred within 48 hours in each of the sixteen cytokines.

Administration of one or more systemic doses can be particularly productive to initiate an immune response, especially in patients with reduced immune capacity. This approach is equally applicable to use of the HX compounds as an immune adjuvant for cancer or microbial infection as is discussed below.

Figure 2:
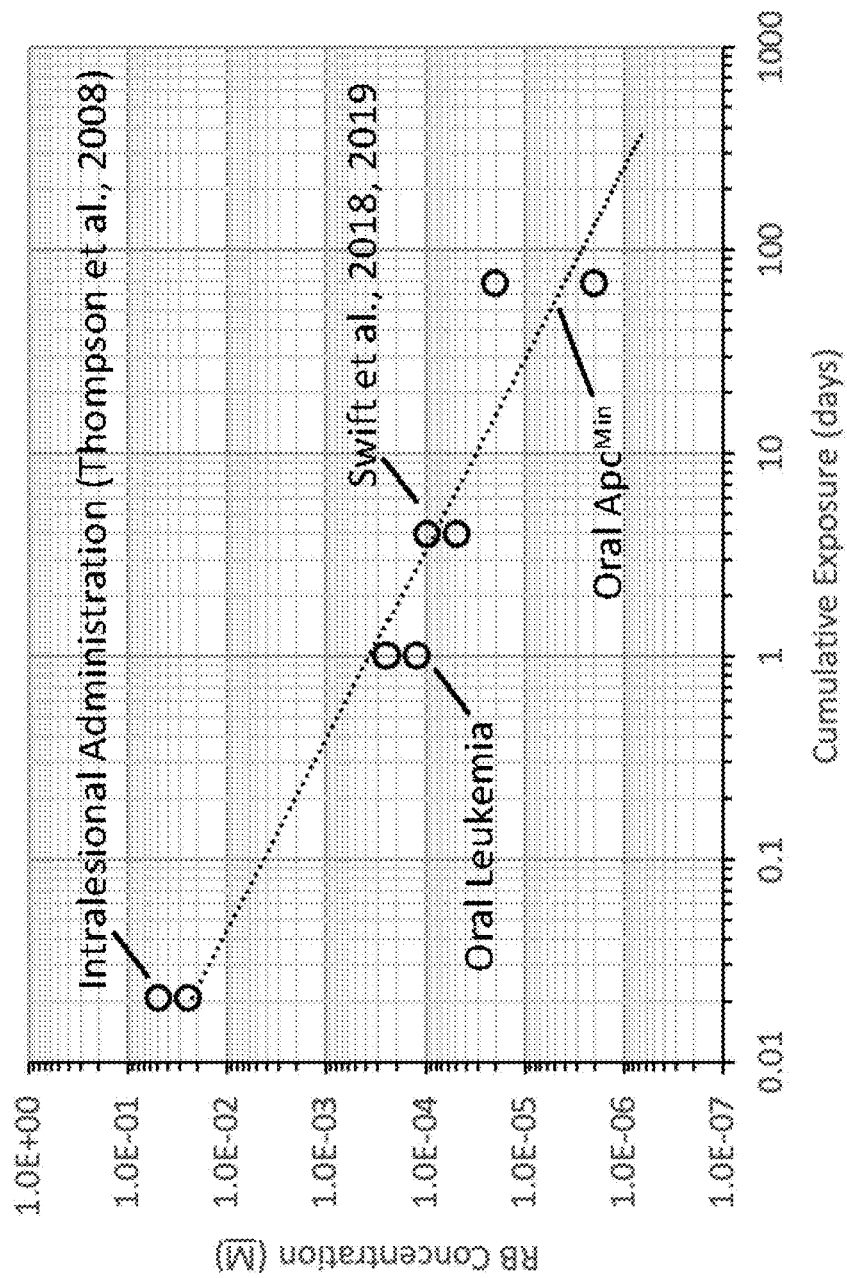
FIG. 2 is a log-log plot of data from several different studies that plots the log of the rose bengal concentration administered (molarity) versus the log of the duration of the HX compound in the subject up to the time of assessing solid tumor treatment, and is also present in an earlier form in U.S. application Ser. No. 17/214,590, filed on Mar. 26, 2021. "Intralesional Administration" represents data present in Thompson et al., *Melanoma Res* 18:405-411 (2008); "Swift 2018, 2019" are from Swift et al., *J Clin Oncol* 36:Suppl; abstr 10557 (2018) and Swift et al., *Oncotargets Ther* 12:1293-1307 (2019); "Oral Apc$^{Min}$" are data from the study reported in International application PCT/US21/024499; and "Oral Leukemia" are data discussed in International application No. PCT/US2021/027702, filed on Apr. 16, 2021.

Dosing—FIG. 2

Upon exposure of tumor cells in a 0.9% sodium chloride-containing aqueous medium to an HX compound, irreversible accumulation of the HX compound occurs in tumor lysosomes, causing immunogenic tumor autolysis once a sufficient concentration is achieved to destabilize lysosomal integrity [Wachter et al., *SPIE* 4620:143-147 (2002)]. This suggests that this immunogenic mechanism of cell death can be elicited over a range of exposure conditions based on a (concentration)·(time function), where cytotoxicity is proportional to the product of these two parameters [i.e., cytotoxicity=f([HX]·t), where "t" is time].

For example, when RB is administered in vivo by intralesional injection to a range of solid tumors (e.g., melanoma, hepatocellular carcinoma, breast carcinoma) acute tumor cytotoxicity is evident within approximately 30 minutes for intratumoral RB concentrations of approximately 25-50 mg/g tumor tissue (25-50 mM) [Thompson et al, *Melanoma Res* 18:405-411 (2008)].

Swift et al. [*Oncotargets Ther* 12:1293-1307 (2019)] demonstrated cytotoxicity of treatment-refractory pediatric solid tumors (neuroblastoma and neuroepithelioma) upon in vitro contact with RB for 96 hours at concentrations of approximately 50-100 µM. Those authors also examined toxicity toward human epithelial cells from three tissue sources and reported $IC_{50}$ values of 93-143 µM. Additionally, Swift et al., [*J Clin Oncol* 36:Suppl; abstr 10557 (2018)], showed cytotoxicity in additional treatment-refractory pediatric solid tumors (Ewing sarcoma, osteosarcoma and rhabdomyosarcoma) under equivalent exposure.

Extended exposure to RB in the context of continuous oral feeding has been shown to prevent formation of colon cancer (prophylactic activity) and to arrest colon cancer (therapeutic activity) in the murine $Apc^{Min}$ colorectal tumor model as disclosed in parental U.S. application Ser. No. 17/214,590, filed on Mar. 26, 2021. For therapeutic use, symptomatic mice receiving RB ad libitum in drinking water at a concentration of 1 mg/mL had an approximate 38% increase in mean survival relative to untreated mice (12.3±0.5 weeks vs 9.8±0.8 weeks). Presuming a daily drinking water consumption rate of approximately 2 mL/10 g body weight, this corresponds to consumption of approximately 2 mg RB/10 g (200 mg/kg).

Bioavailability of RB disodium administered in aqueous solution via the oral route appears to be limited based on mass balance studies conducted by the inventors, and can be estimated at 0.1-1 percent, corresponding to a daily systemic exposure of 0.2-2 mg/kg. Presuming this amount is distributed through the bloodstream, and that blood volume comprises approximately 10 percent of body weight, this equates to an estimated concentration of 2-20 µM RB in the blood.

This same approach was used to plot data presented in FIG. 1 of application PCT/US2021/027702, which shows survival of CB17 SCID mice with established xenografts of a pediatric B acute lymphoblastic leukemia (ALL) tumor cell line; therapeutic activity was observed for mice in two treatment groups receiving RB by gavage twice weekly for two consecutive weeks. Assuming 1% bioavailability of this oral RB, an intestinal transit time of 6 hours per administration, and a blood volume of approximately 10 percent of body weight, the two treatment groups correspond to an estimated 125-250 μM RB in the blood.

Plotting these data confirm that the hypothesized relationship (i.e., cytotoxicity=f([HX]·t)) is supported by experimental results, as illustrated in FIG. 2 of this application.

More importantly, this functional relationship permits prediction of dose level and schedule appropriate to achieve an anti-tumor therapeutic outcome upon systemic administration as well as an adjuvant. For extended systemic treatment schedules equivalent to that investigated with the $Apc^{Min}$ model, low micromolar concentrations (i.e., about 10 μM) of circulating HX compound are sufficient to achieve lysosomal accumulation and tumor cell destruction over a period of approximately 3 months, whereas micromolar to submicromolar concentrations (i.e., about 1 μM) are sufficient to achieve tumor cell destruction over a period of approximately 12 months.

Conversely, shorter duration or interrupted repeat systemic dosing at higher dose level, as used in the oral leukemia model, also achieved cytotoxicity and tumor destruction.

For a specific indication, such as treatment of pediatric patients with leukemia, the relationship of present FIG. 2 illustrates that standard approaches routinely used by those of skill in the art in pharmaceutical development can be applied to select an appropriate dose level and schedule that maximizes therapeutic outcome while minimizing potential safety risk.

Formulary optimization can be guided by standard pharmacokinetic study of absorption such that dose level and formulation are adjusted to achieve the necessary systemic exposure on the desired dose schedule (e.g., about 100 μM in the bloodstream for short duration exposure on the order of several days, about 1 to about 10 μM for intermediate duration exposure on the order of several months, to about <1 μM or lower for long-term exposure on the order of a year or more).

The dibasic salt forms of the HX compounds exist in solution having a pH greater than approximately 5, whereas at pH values <5 the HX compounds spontaneously convert to their lactone form. Because the dibasic salt forms are highly soluble in aqueous media, whereas the lactone forms are insoluble in aqueous media.

The data provided herein illustrate that the $IC_{50}$ value for use of RB against several leukemia cell lines in vitro is about 50 to about 100 μM for exposures of one to several days. Given that the molecular weight of RB disodium is 1018 g/mole, the above $IC_{50}$ value calculates to about 50 to about 100 mg of RB/liter.

Because cytotoxicity due to the HX compound adjuvant is not desired here, an amount less than a cytotoxic amount is used herein, the data in FIG. 2 can be used to provide a ceiling below which an adjuvant-effective amount of a halogenated xanthene can be determined.

The classic intravenous (IV) diagnostic assay for liver function using RB was conducted giving 100 mg RB as a single IV dose. In clinical studies of PV-10® aqueous RB disodium solution, RB has been tolerated at 1500 mg delivered IV. The standard adult blood volume is approximately 5 L. Thus, to achieve 100 mg/L in the blood, an adult patient would need to receive approximately 500 mg of RB IV to achieve the $IC_{50}$ value in the bloodstream. Due to the rapid clearance of RB from circulation ($t_{1/2}$ is about 30 minutes), an IV administration can require continuous infusion to maintain peak levels of RB in circulation (i.e., for up to several hours or more).

The similarly useful halogenated xanthene compounds previously-listed and their pharmaceutically acceptable salts can have molecular weights that differ from each other by about a factor of three (See, Table 3, U.S. Pat. No. 7,390,688 at columns 15-16). It is preferred that an amount of other than RB halogenated xanthene to be used is calculated based on published molecular weights for each such compound and that of RB or RB disodium.

A mammalian subject and to which a mammalian HX compound-adjuvanted vaccine composition is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Halogenated Xanthenes as Immunogen Adjuvants

An alternate, common approach for combating viral infection is the use of an anti-viral vaccine. These medicaments are traditionally predicated on exposing a patient's immune system to moderated or inactivated virus or viral immunogens prior to exposure to live virus via infection. This procedure permits the patient to develop an adaptive immune response capable of preventing significant infection of tropic tissues upon exposure to virus.

Elucidation of the viral genome permits synthetic vaccine development to be undertaken based on modeling viral structure (i.e., surface proteins) to guide identification or synthesis of novel antiviral strategies [Graham et al., *Ann Rev Med* 70:91-104 (2019)]. Publication of the structure of the characteristic SARS-CoV-2 surface spike (S) glycoprotein provided an important target for this type of focused development [Wrapp et al., *Science* 367:1260-1263 (2020)] and led to development of the presently used vaccines.

In particular, the extremely high affinity of RB and its HX compound analogs for glycoproteins conveys potential to: disable viral function by inhibiting attachment of the virus to tropic cells; by inhibiting viral unpacking and replication within infected cells; and as an immune adjuvant by increasing the immunogenicity of virus to the host immune system upon complexation with viral surface glycoprotein structures. Increased immunogenicity can be used during early exposure to potentiate host immune response prior to onset of widespread infection.

Data Regarding Adjuvanticity

Rose bengal disodium has been previously reported to enhance tumor specific immunity in murine models of melanoma and breast. It has also been reported that the enhanced immunity against the tumor (melanoma) after intralesional injection of RB may be due to activation of DCs. In this study, we wanted to further investigate the role of RB in enhancing the CD8-mediated immunity. We chose an in vitro model involving hepatitis B virus infection and studied the effect of RB on CD8 T cell antiviral activity using an interferon gamma ELIspot assay, thus providing an indirect effect of RB Type I IFN-mediated adjuvanticity.

Methodology

PBMC's were isolated from blood from a healthy donor. CD8 cells were magnetically sorted from the PBMC's and cultured in RPMI 10% FBS+IL-7.

The remaining cells were cultured in RPMI 10% FBS+GM-CSF and IL-4 to induce them to become DCs.

After 4-5 days of culture, DCs were pulsed with peptides representing various antigenic regions of hepatitis B virus core protein (HBcAg). The peptides in this study were chosen from academic.oup.com/jid/article/217/5/827/

4705967 research paper that shows that these peptides had the capability to raise CD4 and CD8 T cells against HBV.

After pulsing the DCs with peptides (overnight-about 18 hours), pulsed DCs were co-cultured with CD8 cells in RPMI 10% FBS+IL-2 for 4-5 days. The ratio of DC:CD8 cells was 1:10 for priming to recognize specific antigenic sequences on the DC surface. Rose bengal (5-20 µM) was added in the respective wells during the DC-CD8 co-culture.

After appropriate incubation, primed CD8 cells were co-cultured with PLC/PRF 5 hepatoma cells (1:1 ratio) in RPMI 10% FBS+IL-7 and IL-2 on an IFN-gamma ELIspot plate (R&D Systems, Minneapolis, MN) and incubated for overnight (about 18 hours). PLC/PRF 5 cells are reported to express and secrete HBV particles with accumulation of HBV on the cell surface after 8 days of cell culture.

Results

IFN-gamma is a key moderator of cell-mediated immunity with diverse, mainly pro-inflammatory actions on immunocytes and target tissue. Studies have shown it enhances anti-tumor and antiviral effects of CD8 T cells.

The ELIspot plate was processed the next day (after about 18 hours) according to protocol provided by the manufacturer and spots generated were imaged using an upright, viewed microscopically and counted manually.

Figure 3:
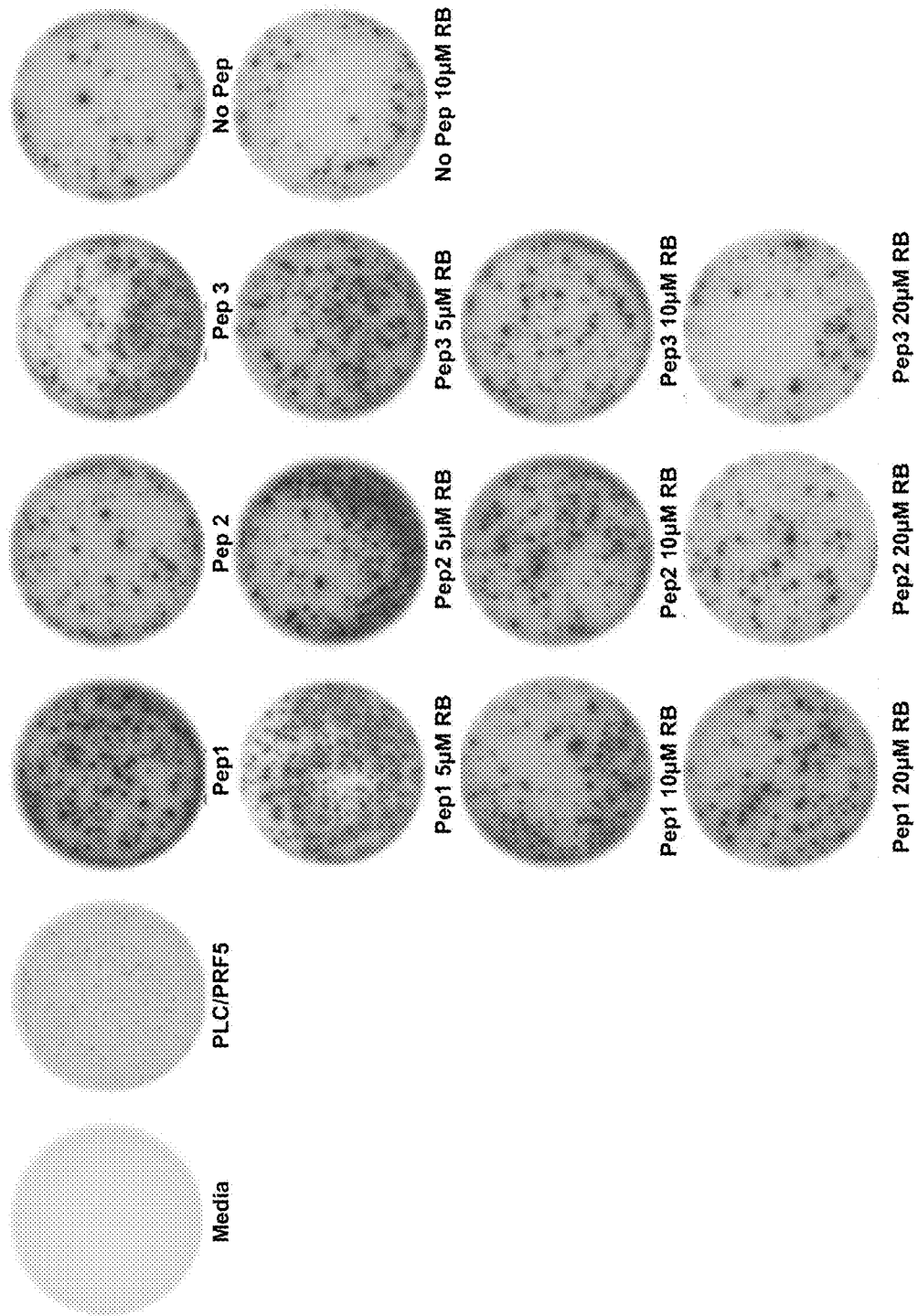
FIG. 3 shows photographic copies of enzyme-linked immunospot plates (ELIspot; R&D Systems, Inc., Minneapolis, MN) of CD8 cells co-cultured with DCs expressing one of the three noted immunogenic peptides (below) hepatitis B virus core protein (HBC) in the presence of equal numbers of PLC/PRF 5 cells in the absence or in the presence of each of the three the stated amounts of rose bengal (RB)

The images obtained show that primed CD8 cells from all three peptide conditions were able to produce higher amount of IFN-gamma as compared to No peptide control (FIG. 3).

Figure 4:
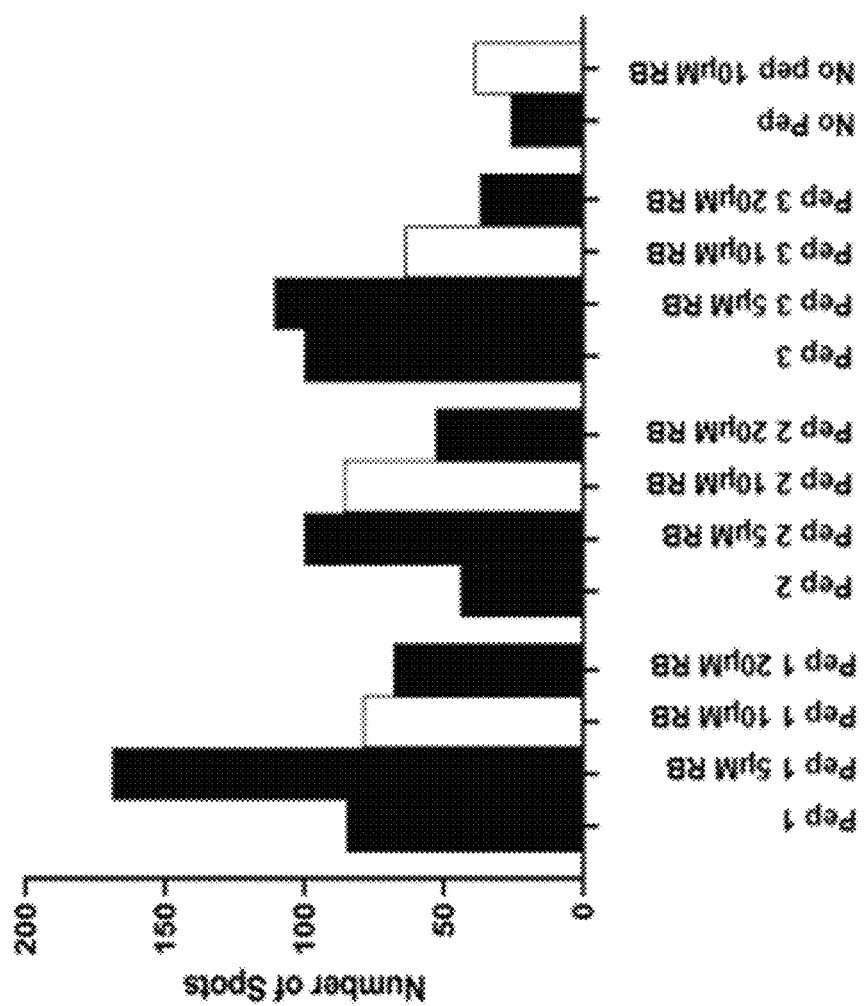

Results show that treatment of 5 µM RB during the CD8-DC co-culture was able to significantly increase the number of IFN-gamma-producing CD8 cells for all three peptides. Increasing the concentration of RB seems to have a negative effect on the cells as the number of IFN-gamma spots decrease with the increasing concentration (FIGS. 3 and 4).

Figure 5:
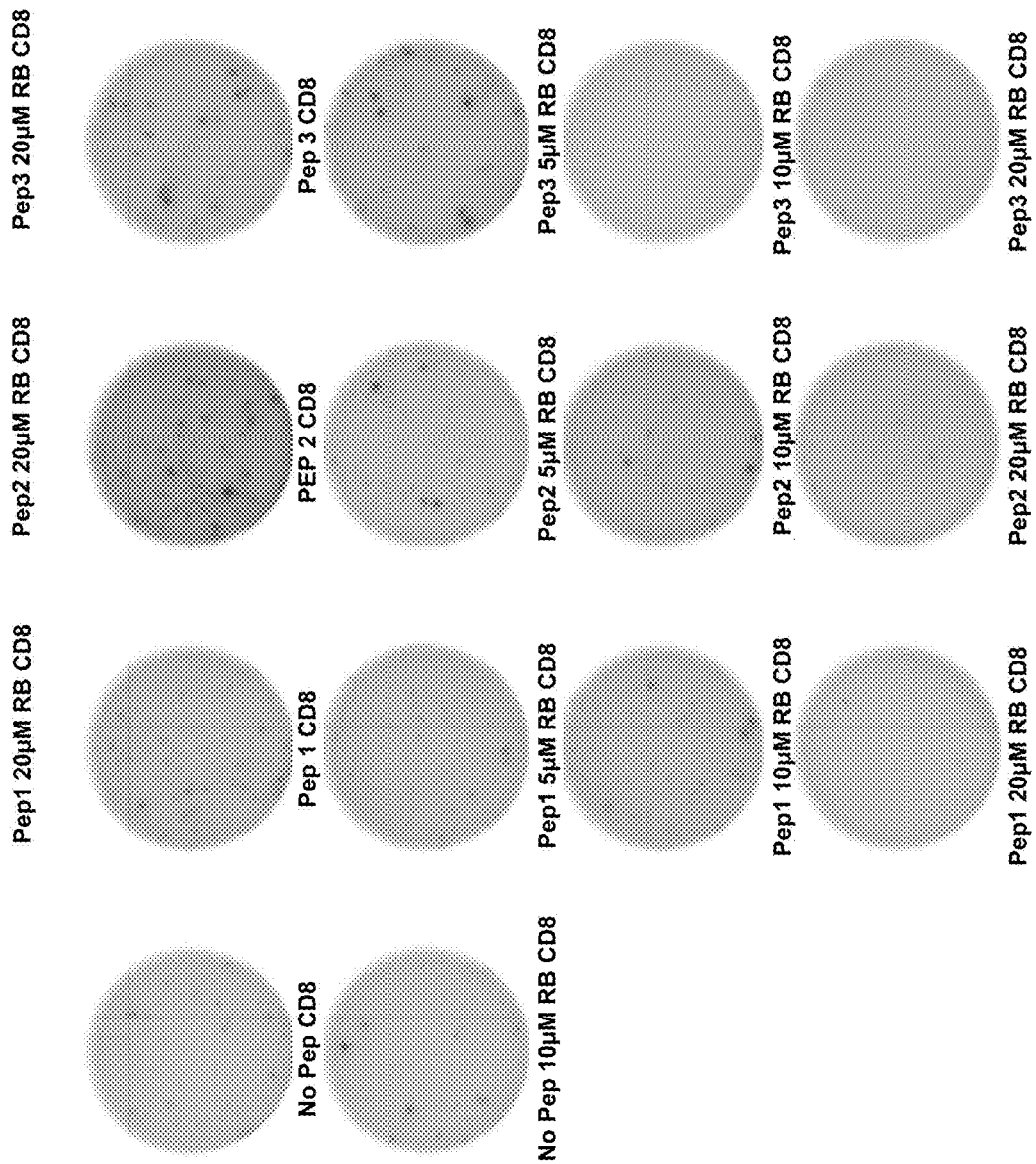

The IFN-gamma spots generated are a result of a specific interaction between CD8 cells primed to recognize specific antigens as fewer number of spots are observed in conditions in which primed CD8 cells alone were incubated on the ELIspot plate without PLC/PRF 5 cells depicting the absence of challenge for these cells (FIG. 5). Those cells were able to produce greater amounts of IFN-gamma when challenged with target cells (PLC/PRF 5 cells in FIG. 3). 5 µM PV-10 appears to induce higher production of IFN-gamma by CD8 cells when they are co-cultured with their target PLC/PRF 5 cells.

The foregoing description and the examples are intended as illustrative and are not to be taken as limiting. Still other variations within the spirit and scope of this invention are possible and will readily present themselves to those skilled in the art.

The invention claimed is:

1. A method of inducing Type I interferon (IFN) response in a mammalian subject that presents with a microbial infection that comprises administering a STING dimerization-inducing amount of a halogenated xanthene (HX), a pharmaceutically acceptable salt, an amide thereof whose nitrogen atom is unsubstituted, substituted with one or two $C_1$-$C_4$ alkyl groups that are the same or different or together with the amido nitrogen form a 5- or 6-membered ring, a $C_1$-$C_4$ alkyl ester thereof, an aromatic derivative thereof, wherein the aromatic derivative is an ester or amide formed from an alcohol or monosubstituted amine having a 5- or 6-membered aromatic ring, or a 5,6- or 6,6-fused aromatic ring system that contains 0, 1 or 2 hetero ring atoms that are independently nitrogen, oxygen or sulfur.

2. The method according to claim 1, wherein said HX is rose bengal disodium.

3. The method according to claim 1, wherein said mammal is a human.

4. The method according to claim 1, wherein said $C_1$-$C_4$ alkyl ester is a $C_2$ ester.

5. The method according to claim 1, wherein said microbial infection is one or more of a viral infection, a bacterial infection, a fungal infection, and a single cell parasitic infection.

6. A method of inducing Type I interferon (IFN) response in a mammalian subject having a cancerous tumor or a hematologic malignancy that comprises systemically administering a STING dimerization-inducing amount of a halogenated xanthene (HX), a pharmaceutically acceptable salt, an amide thereof whose nitrogen atom is unsubstituted, substituted with one or two $C_1$-$C_4$ alkyl groups that are the same or different or together with the amido nitrogen form a 5- or 6-membered ring, a $C_1$-$C_4$ alkyl ester thereof, an aromatic derivative thereof, wherein the aromatic derivative is an ester or amide formed from an alcohol or monosubstituted amine having a 5- or 6-membered aromatic ring, or a 5,6- or 6,6-fused aromatic ring system that contains 0, 1 or 2 hetero ring atoms that are independently nitrogen, oxygen or sulfur.

7. The method according to claim 6, wherein said HX compound is rose bengal disodium.

8. The method according to claim 6, wherein said mammalian subject is a human.

9. The method according to claim 6, wherein said $C_1$-$C_4$ alkyl ester is a $C_2$ ester.

* * * * *